US011097006B2

(12) United States Patent
Perry et al.

(10) Patent No.: US 11,097,006 B2
(45) Date of Patent: *Aug. 24, 2021

(54) PHARMACEUTICAL COMPOSITIONS HAVING IMPROVED STORAGE STABILITY

(71) Applicant: ALKERMES PHARMA IRELAND LIMITED, Dublin (IE)

(72) Inventors: Jason M. Perry, Cambridge, MA (US); Daniel R. Deaver, Franklin, MA (US); Magali B. Hickey, Westwood, MA (US); Julius F. Remenar, Framingham, MA (US); Jennifer Vandiver, Arlington, MA (US); Michael J. Palmieri, Jr., Hopkington, MA (US); Zhengzheng Pan, Arlington, MA (US)

(73) Assignee: ALKERMES PHARMA IRELAND LIMITED, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/834,565

(22) Filed: Mar. 30, 2020

(65) Prior Publication Data

US 2020/0268891 A1    Aug. 27, 2020

Related U.S. Application Data

(60) Continuation of application No. 16/425,150, filed on May 29, 2019, now Pat. No. 10,639,376, which is a continuation of application No. 15/705,237, filed on Sep. 14, 2017, now Pat. No. 10,342,877, which is a division of application No. 14/882,069, filed on Oct. 13, 2015, now Pat. No. 9,861,699, which is a division of application No. 14/031,842, filed on Sep. 19, 2013, now Pat. No. 9,193,685.

(60) Provisional application No. 61/780,862, filed on Mar. 13, 2013, provisional application No. 61/702,881, filed on Sep. 19, 2012.

(51) Int. Cl.
| | |
|---|---|
| *C07D 215/227* | (2006.01) |
| *A61K 47/26* | (2006.01) |
| *A61K 9/00* | (2006.01) |
| *A61K 9/10* | (2006.01) |
| *A61K 31/496* | (2006.01) |
| *A61K 31/5513* | (2006.01) |

(52) U.S. Cl.
CPC ............ *A61K 47/26* (2013.01); *A61K 9/0019* (2013.01); *A61K 9/10* (2013.01); *A61K 31/496* (2013.01); *A61K 31/5513* (2013.01); *C07D 215/227* (2013.01)

(58) Field of Classification Search
CPC .................................................... A61K 47/26
See application file for complete search history.

(56) References Cited

U.S. PATENT DOCUMENTS

| | | |
|---|---|---|
| 2,418,499 A | 4/1947 | Burke |
| 3,266,984 A | 8/1966 | Katsuji |
| 3,523,121 A | 8/1970 | Lewis et al. |
| 3,573,308 A | 3/1971 | Ning et al. |
| 3,957,808 A | 5/1976 | Miller et al. |
| 4,160,099 A | 7/1979 | Bodor |
| 4,204,065 A | 5/1980 | Bodor |
| 4,260,769 A | 4/1981 | Stella |
| 4,428,935 A | 1/1984 | Myers |
| 4,443,464 A | 3/1984 | Biedermann et al. |
| 4,594,190 A | 6/1986 | Giant et al. |
| 4,694,006 A | 9/1987 | Bundgaard et al. |
| 4,727,151 A | 2/1988 | Bodor |
| 4,734,416 A | 3/1988 | Banno et al. |
| 4,760,057 A | 7/1988 | Alexander |
| 4,837,337 A | 6/1989 | Murao et al. |
| 4,914,094 A | 4/1990 | Oshiro et al. |
| 4,992,550 A | 2/1991 | Hughes |
| 5,006,528 A | 4/1991 | Oshiro et al. |
| 5,206,386 A | 4/1993 | Narayanan et al. |
| 5,229,382 A | 7/1993 | Chakrabarti et al. |
| 5,236,927 A | 8/1993 | Jones et al. |
| 5,350,747 A | 9/1994 | Howard |
| 5,462,934 A | 10/1995 | Goto et al. |
| 5,532,372 A | 7/1996 | Saji et al. |
| 5,612,346 A | 3/1997 | Mesens et al. |
| 5,700,946 A | 12/1997 | Shimasaki et al. |
| 5,719,303 A | 2/1998 | Yoshida et al. |
| 5,783,589 A | 7/1998 | Latimer et al. |
| 5,945,416 A | 8/1999 | Shannon et al. |
| 5,985,856 A | 11/1999 | Stella et al. |
| 6,127,357 A | 10/2000 | Cliffe et al. |
| 6,133,248 A | 10/2000 | Stella |
| 6,169,084 B1 | 1/2001 | Bunnell et al. |
| 6,180,095 B1 | 1/2001 | Greenwald et al. |
| 6,608,084 B1 | 8/2003 | Bourzat et al. |
| 6,653,312 B1 | 11/2003 | Auvin et al. |
| 6,656,932 B2 | 12/2003 | Picard et al. |
| 6,977,257 B2 | 12/2005 | Parab et al. |
| 7,053,092 B2 | 5/2006 | Jordan et al. |
| 7,112,603 B2 | 9/2006 | Moon et al. |
| 7,115,587 B2 | 10/2006 | Nerurkar |
| 7,160,888 B2 | 1/2007 | Johnson et al. |

(Continued)

FOREIGN PATENT DOCUMENTS

| | | |
|---|---|---|
| DE | 1273533 B | 7/1968 |
| EP | 0 925 061 B1 | 12/2005 |

(Continued)

OTHER PUBLICATIONS

U.S. Appl. No. 13/423,606 / 2012/0238552 / U.S. Pat. No. 9,034,867, filed Mar. 19, 2012 / Sep. 20, 2012 / May 19, 2015, Jason M. Perry.

(Continued)

*Primary Examiner* — Paul V Ward
(74) *Attorney, Agent, or Firm* — Brian C. Trinque; Lathrop GPM LLP

(57) ABSTRACT

The present invention relates to a pharmaceutical composition that provides long-term stability of a hydrolytically labile antipsychotic agent

15 Claims, 6 Drawing Sheets

(56) References Cited

U.S. PATENT DOCUMENTS

| | | |
|---|---|---|
| 7,374,779 B2 | 5/2008 | Chen et al. |
| 7,538,121 B2 | 5/2009 | MacDonald et al. |
| 7,550,445 B2 | 6/2009 | Nerurkar et al. |
| 7,807,680 B2 | 10/2010 | Kostanski et al. |
| 7,910,577 B2 | 3/2011 | Liversidge et al. |
| 7,981,906 B2 | 7/2011 | Dull et al. |
| 8,017,515 B2 | 9/2011 | Marimuthu et al. |
| 8,017,615 B2 | 9/2011 | Bando et al. |
| 8,030,313 B2 | 10/2011 | Kostanski et al. |
| 8,338,427 B2 | 12/2012 | Brown |
| 8,338,428 B2 | 12/2012 | Brown |
| 8,399,469 B2 | 3/2013 | Banda et al. |
| 8,431,576 B2 | 4/2013 | Remenar et al. |
| 8,518,421 B2 | 8/2013 | Kothari et al. |
| 8,536,328 B2 | 9/2013 | Remenar et al. |
| 8,580,796 B2 | 11/2013 | Banda et al. |
| 8,642,600 B2 | 2/2014 | Jordan et al. |
| 8,642,760 B2 | 2/2014 | Banda et al. |
| 9,034,867 B2 | 5/2015 | Perry et al. |
| 9,193,685 B2 * | 11/2015 | Perry ............... A61P 25/00 |
| 9,351,976 B2 | 5/2016 | Perry et al. |
| 9,452,131 B2 | 9/2016 | Hickey et al. |
| 9,526,726 B2 | 12/2016 | Hickey et al. |
| 2002/0146455 A1 | 10/2002 | Kundu et al. |
| 2002/0176841 A1 | 11/2002 | Barker et al. |
| 2003/0064998 A1 | 4/2003 | Francois et al. |
| 2003/0077297 A1 | 4/2003 | Chen et al. |
| 2004/0101557 A1 | 5/2004 | Gibson et al. |
| 2005/0019436 A1 | 1/2005 | Burch et al. |
| 2005/0032811 A1 | 2/2005 | Brown et al. |
| 2005/0079185 A1 | 4/2005 | Parisot et al. |
| 2005/0203089 A1 | 9/2005 | Starrett, Jr. et al. |
| 2005/0282821 A1 | 12/2005 | Lesur et al. |
| 2006/0040922 A1 | 2/2006 | Greco et al. |
| 2006/0142333 A1 | 6/2006 | MacDonald et al. |
| 2006/0154918 A1 | 7/2006 | Liversidge et al. |
| 2006/0194345 A1 | 8/2006 | Uchiyama et al. |
| 2006/0293217 A1 | 12/2006 | Barker et al. |
| 2007/0031513 A1 | 2/2007 | Kikuchi et al. |
| 2007/0148100 A1 | 6/2007 | Jenkins |
| 2007/0191611 A1 | 8/2007 | Rao et al. |
| 2008/0085888 A1 | 4/2008 | Breining et al. |
| 2008/0186971 A1 | 8/2008 | Carmichael et al. |
| 2008/0233053 A1 | 9/2008 | Gross et al. |
| 2008/0261954 A1 | 10/2008 | Maelicke |
| 2008/0312199 A1 | 12/2008 | Glinsky |
| 2008/0318905 A1 | 12/2008 | Muhammad et al. |
| 2009/0053329 A1 | 2/2009 | Peter et al. |
| 2009/0068290 A1 | 3/2009 | Bourin et al. |
| 2009/0118242 A1 | 5/2009 | Burch et al. |
| 2009/0143403 A1 | 6/2009 | Brown |
| 2009/0163519 A1 | 6/2009 | Vermeulen et al. |
| 2009/0163545 A1 | 6/2009 | Goldfarb |
| 2009/0169632 A1 | 7/2009 | Lu et al. |
| 2009/0311347 A1 | 12/2009 | Oronsky et al. |
| 2010/0197641 A1 | 8/2010 | Mazess et al. |
| 2010/0203129 A1 | 8/2010 | Andersen et al. |
| 2010/0286136 A1 | 11/2010 | Jones et al. |
| 2010/0292316 A1 | 11/2010 | Sanders et al. |
| 2010/0331356 A1 | 12/2010 | Legen et al. |
| 2011/0003828 A1 | 1/2011 | Blumberg |
| 2011/0015156 A1 | 1/2011 | Remenar et al. |
| 2011/0105536 A1 | 5/2011 | Lewyn-Briscoe et al. |
| 2011/0166128 A1 | 7/2011 | Remenar et al. |
| 2011/0166156 A1 | 7/2011 | Blumberg et al. |
| 2011/0166194 A1 | 7/2011 | Blumberg et al. |
| 2011/0178068 A1 | 7/2011 | Almarsson et al. |
| 2011/0195095 A1 | 8/2011 | Liversidge et al. |
| 2011/0236478 A1 | 9/2011 | Dokou et al. |
| 2011/0275803 A1 | 11/2011 | Remenar et al. |
| 2011/0319422 A1 | 12/2011 | Blumberg et al. |
| 2012/0015866 A1 | 1/2012 | Blumberg et al. |
| 2012/0238552 A1 | 9/2012 | Perry et al. |
| 2013/0003046 A1 | 1/2013 | Izawa et al. |
| 2013/0096089 A1 | 4/2013 | Remenar et al. |
| 2013/0267503 A1 | 10/2013 | Perry et al. |
| 2013/0267504 A1 | 10/2013 | Perry et al. |
| 2013/0267505 A1 | 10/2013 | Perry et al. |
| 2015/0258115 A1 | 9/2015 | Perry et al. |
| 2015/0265529 A1 | 9/2015 | Hickey et al. |
| 2016/0038508 A1 | 2/2016 | Perry et al. |
| 2016/0263111 A1 | 9/2016 | Hickey et al. |
| 2017/0157117 A1 | 6/2017 | Hickey et al. |
| 2017/0196856 A1 | 7/2017 | Perry et al. |

FOREIGN PATENT DOCUMENTS

| | | |
|---|---|---|
| EP | 1 891 956 A1 | 2/2008 |
| GB | 0 849 541 A | 9/1960 |
| GB | 2 017 701 A | 10/1979 |
| GB | 2 054 371 A | 2/1981 |
| JP | S60-002331 A | 1/1985 |
| WO | 1990/014080 A1 | 11/1990 |
| WO | 1991/000863 A1 | 1/1991 |
| WO | 1993/025197 A1 | 12/1993 |
| WO | 1996/012725 A1 | 5/1996 |
| WO | 1997/043284 A1 | 11/1997 |
| WO | 1999/033846 A2 | 7/1999 |
| WO | 2002/049573 A2 | 6/2002 |
| WO | 2002/096351 A2 | 12/2002 |
| WO | 2004/012671 A1 | 2/2004 |
| WO | 2004/026864 A1 | 4/2004 |
| WO | 2004/067546 A1 | 8/2004 |
| WO | 2004/089925 A1 | 10/2004 |
| WO | 2005/016262 A2 | 2/2005 |
| WO | 2005/066165 A1 | 7/2005 |
| WO | 2005/079807 A1 | 9/2005 |
| WO | 2006/037090 A1 | 4/2006 |
| WO | 2006/055603 A2 | 5/2006 |
| WO | 2006/090273 A2 | 8/2006 |
| WO | 2007/018943 A2 | 2/2007 |
| WO | 2007/059111 A2 | 5/2007 |
| WO | 2008/124030 A1 | 10/2008 |
| WO | 2009/052467 A1 | 4/2009 |
| WO | 2009/060473 A2 | 5/2009 |
| WO | 2010/135703 A2 | 11/2010 |
| WO | 2010/151689 A1 | 12/2010 |
| WO | 2010/151711 A1 | 12/2010 |
| WO | 2011/084846 A1 | 7/2011 |
| WO | 2011/084848 A2 | 7/2011 |
| WO | 2012/129156 A1 | 9/2012 |
| WO | 2013/142198 A1 | 9/2013 |
| WO | 2013/142202 A1 | 9/2013 |
| WO | 2013/142205 A1 | 9/2013 |
| WO | 2014/080285 A2 | 5/2014 |
| WO | 2015/143145 A1 | 9/2015 |

OTHER PUBLICATIONS

U.S. Appl. No. 14/688,050 / 2016/0038508, filed Apr. 16, 2015 / Feb. 11, 2016, Jason M. Perry.
U.S. Appl. No. 14/714,621 / 2015/0258115 / U.S. Pat. No. 9,351,976, filed May 18, 2015 / Sep. 17, 2015 / May 31, 2016, Jason M. Perry.
U.S. Appl. No. 15/154,562, filed May 13, 2016, Jason M. Perry.
U.S. Appl. No. 15/388,554/ 2017/0196856 / U.S. Pat. No. 10,226,458, filed Dec. 22, 2016 / Jul. 13, 2017 / Mar. 12, 2019, Jason M. Perry.
U.S. Appl. No. 16/248,259 / 2019/0216805, filed Jan. 15, 2019 / Jul. 18, 2019, Jason M. Perry.
U.S. Appl. No. 13/801,025 / 2013/0267503, filed Mar. 13, 2013 / Oct. 10, 2013, Jason M. Perry.
U.S. Appl. No. 13/801,167 / 2013/0267504, filed Mar. 13, 2013 / Oct. 10, 2013, Jason M. Perry.
U.S. Appl. No. 13/801,344 / 2013/0267505, filed Mar. 13, 2013 / Oct. 10, 2013, Jason M. Perry.
U.S. Appl. No. 14/031,842 / 2014/0088115 / U.S. Pat. No. 9,193,685, filed Sep. 19, 2013 / Mar. 27, 2014 / Nov. 24, 2015, Jason M. Perry.
U.S. Appl. No. 14/882,069 / 2016/0136279 / U.S. Pat. No. 9,861,699, filed Oct. 13, 2015 / May 19, 2016 / Jan. 9, 2018, Jason M. Perry.
U.S. Appl. No. 16/425,150 / 2019/0275155 / U.S. Pat. No. 10,639,376, filed May 29, 2019 / Sep. 12, 2019 / May 5, 2020, Jason M. Perry.
U.S. Appl. No. 16/834,565, filed Mar. 30, 2020, Jason M. Perry.

(56) References Cited

OTHER PUBLICATIONS

U.S. Appl. No. 15/705,237 / 2018/0000944 / U.S. Pat. No. 10,342,877, filed Sep. 14, 2017/ Jan. 4, 2018 / Jul. 9, 2019, Jason M. Perry.
U.S. Appl. No. 14/663,042 / 2015/0265529 / U.S. Pat. No. 9,452,131, filed Mar. 19, 2015 / Sep. 24, 2015 / Sep. 27, 2016, Magali B. Hickey.
U.S. Appl. No. 15/164,473 / 2016/0263111 / U.S. Pat. No. 9,526,726, filed May 25, 2016 / Sep. 15, 2016 / Dec. 27, 2016, Magali B. Hickey.
U.S. Appl. No. 15/349,243 / 2017/0157117 / U.S. Pat. No. 10,085,980, filed Nov. 11, 2016 / Jun. 8, 2017 / Oct. 2, 2018, Magali B. Hickey.
U.S. Appl. No. 16/116,652 / 2018/0369239 / U.S. Pat. No. 10,238,651, filed Aug. 29, 2018 / Dec. 27, 2018 / Mar. 26, 2019, Magali B. Hickey.
U.S. Appl. No. 16/271,248 / 2019/0167673, filed Feb. 8, 2019 / Jun. 6, 2019, Magali B. Hickey.
U.S. Appl. No. 16/889,528, filed Jun. 1, 2020, Magali B. Hickey.
Akers et al. (1987) "Formulation Design and Development of Parenteral Suspensions," Journal Parenteral Science and Technology. 41(3):88-96.
Belikov (1993) "химия: Общая Фа рм а цевтическая химия [General Chemistry: Pharmaceutical Chemistry]," Part 1. Moscow, Russia. pp. 43-45.—with English machine translation.
Blakenship et al. (2010) "Aripiprazole for irritability associated with autistic disorder in children and adolescents aged 6-17 years," Ped. Health. 4(4):375-381.
Chang et al. (1996) "Development of a stable freeze-dried formulation of recombinant human interleukin-1 receptor antagonist," Pharm. Res. 13:243-249.
Chueshov (2002) "[Industrial technology of medicaments]," vol. 1. p. 24—with English machine translation.
Cocoman et al. (2008) "Intramuscular injections: a review of best practice for mental health nurses," Journal of Psychiatric and Mental Health Nursing. 15:424-434.
Dai et al. (2007) "Parallel screening approach to identify solubility-enhancing formulations for improved bioavailability pf a poorly water-soluble compound using milligram quantities of material," International Journal of Pharmaceutics. 336:1-11.
Lieberman et al.: Eds. (1997) Pharmaceutical Dosage Forms: Disperse Systems. vol. 2. pp. 18-22, 285-301.
Mackenzie (1977) "Non-Equilibrium Freezing Behaviour of Aqueous Systems [and Discussion]," Philosophical Transactions of the Royal Society of London. 278(959):167-189.
Park et al. (1999) "Preparation and evaluation of flurbiprofen-loaded microemulsion for parenteral delivery," International Journal of Pharmaceutics. 181(2):173-179.
Pearson Education, Inc. (1995) "Medication Adminstration Techniques: Injections," [Last Accessed Oct. 30, 2015].
Porras et al. (2004) "Studies of formation of W/O nano-emulsions," Colloids and Surfaces A: Physicochem. Eng. Aspects. 249:115-118.
Shinde et al. (2011) "Microemulsions and Nanoemulsions for Targeted Drug Delivery to the Brain," Current Nanoscience. 7:119-133.
Shintani et al. (1967) "A new method to determine the irritation of drugs after intramuscular injection in rabbits," Toxicology and Applied Pharmacology. 11(2):293-295.
Strickley et al. (2004) "Solubilizing Excipients in Oral and Injectable Formulations," Pharmaceutical Research. 21(2):201-230.
Tang et al. (2004) "Design of freeze-drying processes for pharmaceuticals: practical advice," Pharm. Res. 21:191-200.
Workman (1999) "Safe injection techniques," Nursing Standard. 13(39):47-53.
World Health Organization (2003) "Annex 9: Guide to good storage practices for pharmaceuticals," WHO Technical Report Series, No. 908.
International Preliminary Report on Patentability corresponding to International Patent Application No. PCT/US2012/029625, dated Sep. 24, 2013.
International Search Report with Written Opinion corresponding to International Patent Application No. PCT/IB2013/002995, dated Jun. 11, 2014.
International Search Report with Written Opinion corresponding to International Patent Application No. PCT/US2012/029625, dated Aug. 18, 2012.
International Search Report with Written Opinion corresponding to International Patent Application No. PCT/US2013/030905, dated Jun. 26, 2013.
International Search Report with Written Opinion corresponding to International Patent Application No. PCT/US2013/030916, dated Aug. 26, 2013.
International Search Report with Written Opinion corresponding to International Patent Application No. PCT/US2013/030933, dated Jun. 26, 2013.
International Search Report with Written Opinion corresponding to International Patent Application No. PCT/US2013/030945, dated Jun. 27, 2013.
International Search Report with Written Opinion corresponding to International Patent Application No. PCT/US2013/060677, dated Jan. 10, 2014.
International Search Report with Written Opinion corresponding to International Patent Application No. PCT/US2015/021448, dated Jun. 19, 2015.

\* cited by examiner

In vitro (standing) hydrolysis of Aripiprazole prodrug

Figure 3
25 °C/60% RH Data Summary for Compound 1

| | | Initial | 1M | 3M | 6M | 9M | 12M | 18M | 24M |
|---|---|---|---|---|---|---|---|---|---|
| Description | | Vial Package: Colorless glass vial with a gray rubber concave stopper and a seal with a flip-off cap / Product: White suspension | | | | | | | |
| Dose Delivery (mg/mL) (239-292 mg/mL) | | 259 | 258 | 257 | 267 | 258 | 251 | 263 | 269 |
| Total Related Impurities | | 0.20% | 0.25% | 0.24% | 0.23% | 0.20% | 0.21% | 0.20% | 0.21% |
| Single Largest Impurity | | 0.10% | 0.12% | 0.12% | 0.10% | 0.10% | 0.10% | 0.10% | 0.09% |
| PSD | Dv[10] | 6 μm | 5 μm | 7 μm | 5 μm | 5 μm | 6 μm | 9 μm | 8 μm |
| | Dv[50] | 19 μm | 19 μm | 23 μm | 20 μm | 20 μm | 21 μm | 25 μm | 26 μm |
| | Dv[90] | 47 μm | 47 μm | 49 μm | 51 μm | 50 μm | 48 μm | 48 μm | 51 μm |
| pH (5.0-7.4) | | 6.8 | 6.8 | 6.8 | 6.8 | 6.8 | 6.8 | 6.7 | 6.7 |
| IV Initial Release | Aripiprazole + N-hydroxymethyl aripiprzole | <5 ppm | <5 ppm | <5 ppm | <5 ppm | 6 ppm | 6 ppm | 14 ppm | 22 ppm |
| | Compound 1 | 67 ppm | 55 ppm | 31 ppm | 38 ppm | 39 ppm | 40 ppm | 43 ppm | 43 ppm |
| Injectability | | 6 | 7 | 6 | 6 | 5 | 6 | Not Tested | Not Tested |
| Lauric Acid | | ND | ND | ND | ND | ND | ND | 0.06% | 0.07% |

Figure 4
40 °C/75% RH Data Summary for Compound 1

| | | Initial | 1M | 3M | 6M |
|---|---|---|---|---|---|
| Description | | \multicolumn{4}{l}{Vial Package: Colorless glass vial with a gray rubber concave stopper and a seal with a flip-off cap Product: White suspension} | | | |
| Dose Delivery (mg/mL) (239-292 mg/mL) | | 259 | 266 | 260 | 267 |
| Total Related Impurities | | 0.20% | 0.24% | 0.24% | 0.22% |
| Single Largest Impurity | | 0.10% | 0.12% | 0.12% | 0.10% |
| PSD | Dv[10] | 6 μm | 6 μm | 9 μm | 6 μm |
| | Dv[50] | 19 μm | 21 μm | 26 μm | 21 μm |
| | Dv[90] | 47 μm | 50 μm | 51 μm | 51 μm |
| pH (5.0-7.4) | | 6.8 | 6.7 | 6.7 | 6.7 |
| IV Initial Release | Aripiprazole + N-hydroxymethyl aripiprzole | <5 ppm | <5 ppm | <5 ppm | 16 ppm |
| | Compound 1 | 67 ppm | 43 ppm | 5 ppm | 11 ppm |
| Injectability | | 6 | 6 | 5 | 6 |
| Lauric Acid | | ND | ND | 0.05% | 0.08% |

Figure 5
30 °C/75% RH Data Summary for Compound 1

|  |  | Initial | 6M | 12M | 24M |
|---|---|---|---|---|---|
| Description | | Vial Package: Colorless glass vial with a gray rubber concave stopper and a seal with a flip-off cap<br>Product: White suspension | | | |
| Dose Delivery (mg/mL) (239-292 mg/mL) | | 259 | 275 | 271 | 274 |
| Total Related Impurities | | 0.20% | 0.22% | 0.21% | 0.21% |
| Single Largest Impurity | | 0.10% | 0.10% | 0.10% | 0.10% |
| PSD | Dv[10] | 6 µm | 6 µm | 6 µm | 8 µm |
| | Dv[50] | 19 µm | 21 µm | 20 µm | 27 µm |
| | Dv[90] | 47 µm | 54 µm | 47 µm | 57 µm |
| pH (5.0-7.4) | | 6.8 | 6.8 | 6.7 | 6.6 |
| IV Initial Release | Aripiprazole + N-hydroxymethyl aripiprzole | < 5 ppm | < 5 ppm | 6 ppm | 24 ppm |
| | Compound 1 | 67 ppm | 7 ppm | 18 ppm | 19 ppm |
| Injectability | | 6 | 7 | 6 | Not Tested |
| Lauric Acid | | ND | ND | 0.06% | 0.11% |

Figure 6
40°C/75% RH Data for Compound 1

|  |  | Initial | 1M | 3M | 6M |
|---|---|---|---|---|---|
| Complete Release | 6 hrs | 14% | 11% | 13% | 15% |
|  | 24 hrs | 46% | 41% | 44% | 49% |
|  | 30 hrs | 54% | 49% | 52% | 57% |
|  | 48 hrs | 73% | 66% | 70% | 74% |
|  | 72 hrs | 88% | 83% | 84% | 87% |
|  | 96 hrs | 96% | 92% | 92% | 96% |
|  | 120 hrs | 103% | 97% | 98% | 101% |
| Surface Area |  | 0.94 m$^2$/g |  |  |  |
| Aldehydes | Formaldehyde | 0.9 ppm | 3.7 ppm | 6.0 ppm | 11.7 ppm |
|  | Acetaldehyde | 1.6 ppm | 2.2 ppm | 2.4 ppm | 2.0 ppm |
|  | Acetone | ND | <1 ppm | <1 ppm | ND |
|  | Propionaldehyde | ND | <1 ppm | <1 ppm | ND |

PHARMACEUTICAL COMPOSITIONS HAVING IMPROVED STORAGE STABILITY

RELATED APPLICATION

This application claims priority to U.S. Provisional Application No. 61/702,881, filed Sep. 19, 2012 and to U.S. Provisional Application No. 61/780,862, filed Mar. 13, 2013. The entire contents of these applications are incorporated herein by reference in their entireties.

TECHNICAL FIELD

The present invention relates to a pharmaceutical composition that provides long-term stability of a hydrolytically labile antipsychotic agent.

BACKGROUND OF THE INVENTION

U.S. Pat. Nos. 4,734,416 and 5,006,528 disclose aripiprazole, 7-{4-[4-(2,3-dichlorophenyl)-1-piperazinyl]butoxy}-3,4-dihydro-2(1H)-quinolinone or 7-{4-[4-(2,3-dichlorophenyl)-1-piperazinyl]butoxy}-3,4-dihydro carbostyril, as an atypical antipsychotic agent useful in the treatment of schizophrenia, bipolar disease, depression and other CNS disorders. Aripiprazole has the following chemical structure:

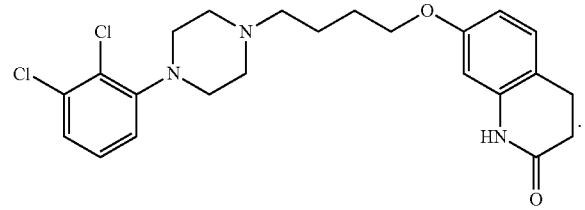 [SMILES: O=C1CCc2ccc(OCCCCN3CCN(c4cccc(Cl)c4Cl)CC3)cc2N1]

Aripiprazole is sold under the tradename Ability®. It acts as a dopamine $D_2$ partial agonist, serotonin 5-$HT_{1A}$ receptor agonist and is an antagonist of the serotonin 5-$HT_{2A}$ receptor. Abilify® is currently administered orally on a once-a-day dosing schedule as Abilify® (aripiprazole) Tablets, Abilify Discmelt® (aripiprazole) Orally Disintegrating Tablets and Abilify® (aripiprazole) Oral Solution. In one embodiment, Abilify® Injection for intramuscular use is a rapid-acting solution product for treating agitation associated with schizophrenia and bipolar disease. Poor and variable patient compliance with a once-a-day dosing schedule of psychiatric drugs has been reported.

Olanzapine (1,2-methyl-4-(4-methyl-1-piperazinyl)-10H-thieno[2,3-b][1,5]benzodiazepine) is a second generation antipsychotic drug marketed as Zyprexa®. It is useful for the treatment of disorders such as schizophrenia, bipolar disorder, psychotic depression, and Tourette syndrome. This active pharmaceutical ingredient acts as an antagonist on 5-$HT_2$ serotonin receptors as well as the $D_1/D_2$ dopamine receptors, while also exhibiting anticholinergic and antimuscarinic properties. Olanzapine belongs to the benzodiazepine family, and has the following structure:

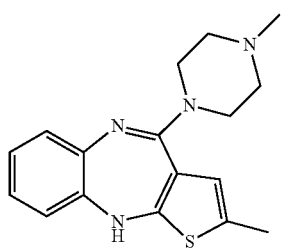

This compound is disclosed, for example, in U.S. Pat. Nos. 5,229,382 and 6,169,084. An extended release intramuscular injection product containing the water-insoluble salt olanzapine pamoate monohydrate is approved for use in schizophrenia.

Long-term stability is a critical consideration of drug formulation, expiry, shelf-life, and manufacturing. As such, stable pharmaceutical formulations that do not result in drug degradation of these and other antipsychotics through, e.g., hydrolysis and/or oxidation, are desired.

SUMMARY OF THE INVENTION

Provided herein are pharmaceutical compositions comprising: (a) a hydrolytically labile antipsychotic agent; (b) a non-ionic water insoluble and/or immiscible ester co-surfactant; (c) a water miscible and/or soluble non-ionic surfactant; and (d) an aqueous vehicle; wherein the pharmaceutical composition comprises a minimal amount of the antipsychotic hydrolysis products after standing for a certain period of time. In an embodiment, the pharmaceutical composition comprises a minimal amount of the antipsychotic hydrolysis products after standing for a certain period of time at various temperature and humidity conditions. For example, the pharmaceutical composition can comprise less than 50 parts per million, e.g., less than 30 parts per million, e.g., less than 10 parts per million, after standing for up to, or more than, 24 months. In an embodiment, the pharmaceutical composition comprises less than 50 parts per million, e.g., less than 30 parts per million, e.g., less than 10 parts per million, of the hydrolyzed antipsychotic agent degradation products after standing for at least 1 month, 3 months, 6 months, 9 months, 12 months, 18 months, or 24 months.

In an embodiment, the pharmaceutical composition comprises less than 50 parts per million, e.g., less than 30 parts per million, e.g., less than 10 parts per million, of the hydrolyzed antipsychotic agent degradation products at certain temperature and humidity conditions, such as 25° C., with a relative humidity of 60%; 40° C., with a relative humidity of 75%; or 30° C., with a relative humidity of 75%. In an embodiment, the pharmaceutical composition comprises less than 50 parts per million, e.g., less than 30 parts per million, e.g., less than 10 parts per million, of the hydrolyzed antipsychotic agent degradation products at temperatures of 25° C.-40° C. In an embodiment, the degradation is minimized at temperatures selected from any of 25° C.-40° C., over a time period selected from any of 1 month-24 months, e.g., at least 1 month, 3 months, 6 months, 9 months, 12 months, 18 months, or 24 months. In other embodiments, the pharmaceutical composition comprises less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 parts per million of the hydrolyzed antipsychotic agent degradation products at temperatures of 25° C.-40° C.

In an embodiment, the non-ionic water insoluble and/or immiscible ester co-surfactant is a sorbitan ester of a carboxylic acid, wherein the carboxylic acid comprises 4-20 carbon atoms. A non-limiting example of this sorbitan ester is sorbitan laurate. In another embodiment, the water miscible and/or soluble non-ionic surfactant is a polyoxyethylene derivative of a sorbitan ester of a carboxylic acid, wherein the carboxylic acid comprises 8-14 carbon atoms. A non-limiting example of such a polyoxyethylene derivative of a sorbitan ester is polysorbate 20.

As described herein, the hydrolytically labile antipsychotic agent can be any number of antipsychotic compounds that are susceptible to hydrolysis. In certain embodiments, the compounds are in prodrug form. In one embodiment, the antipsychotic agent is selected from the group consisting of an aripiprazole prodrug (e.g., a compound of Formula I or II), or olanzapine prodrug (e.g., a compound of Formula III, IV or V). Non-limiting examples of such compounds are provided below, as Compound A or Compound 1:

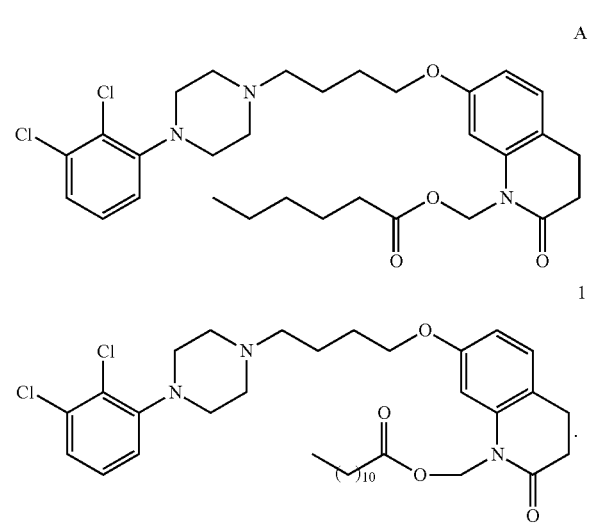

In an embodiment of the pharmaceutical composition, the hydrolyzed drug product that is formed to a minimal extent can be the aripiprazole drug form:

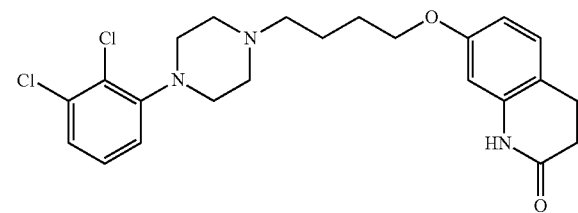 [SMILES: O=C1CCc2ccc(OCCCCN3CCN(c4cccc(Cl)c4Cl)CC3)cc2N1]

and/or the N-methylene hydroxy compound having the following formula (referred to herein as "the N-hydroxymethyl compound" or "N-hydroxymethyl aripiprazole"):

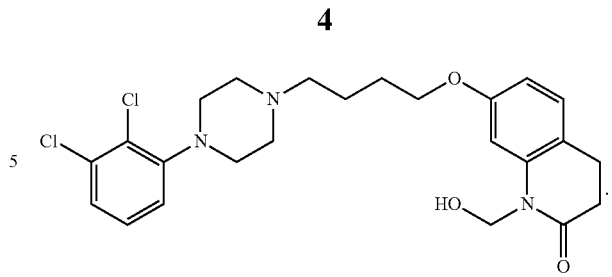

In a particular embodiment of the pharmaceutical composition, the majority of the antipsychotic agent is dissolved within the non-ionic water insoluble and/or immiscible ester co-surfactant. In another particular embodiment of the pharmaceutical composition, the antipsychotic agent is dissolved within the non-ionic water insoluble and/or immiscible ester co-surfactant.

In an embodiment, the pharmaceutical composition is injectable. Furthermore, the compositions can be easily resuspended by the user, e.g., through handshaking, in a short time prior to administration. Accordingly, because the pharmaceutical composition does not require reconstitution (i.e., addition of injection vehicle to drug powder prior to use), the pharmaceutical composition can be referred to herein as "ready to use."

The composition comprising components (b) and (c) can have these components at varying ratios. In a particular embodiment, the ratio of components (b) to (c) is approximately 5 to 2, by weight.

The composition can comprise about 0.2-1 weight percent, about 0.4-0.7 weight percent, or about 0.5 weight percent component (b). When component (b) is sorbitan laurate, the composition can comprise about 0.2-1 weight percent, about 0.4-0.7 weight percent, or about 0.5 weight percent sorbitan laurate. In an embodiment, the composition comprises not more than 0.5 weight percent sorbitan laurate.

The composition also can comprise about 0.25-0.45 weight percent, about 0.3-0.4 weight percent, or about 0.37 weight percent component (b). When component (b) is sorbitan laurate, the composition also can comprise about 0.25-0.45 weight percent, about 0.3-0.4 weight percent, or about 0.37 weight percent sorbitan laurate. In a particular embodiment, the composition comprises about 0.37 weight percent sorbitan laurate.

The composition can comprise about 0.05-0.8 weight percent polysorbate 20, about 0.1-0.3 weight percent polysorbate 20, about 0.2 weight percent, or about 0.15 weight percent component (c). When component (c) is polysorbate 20, the composition can comprise about 0.05-0.8 weight percent polysorbate 20, about 0.1-0.3 weight percent polysorbate 20, about 0.2 weight percent, or about 0.15 weight percent polysorbate 20. In a particular embodiment, the composition comprises about 0.15 weight percent polysorbate 20.

The compositions can have varying amounts of antipsychotic agent in the pharmaceutical composition. For example, the composition can be comprised of 15-35 weight percent, e.g., 20-30 weight percent, e.g., 20-26 weight percent antipsychotic agent. In an embodiment, the composition can be comprised of 15-35 weight percent, e.g., 20-30 weight percent, e.g., 20-26 weight percent aripiprazole prodrug (e.g., a compound of Formula I or II), or olanzapine prodrug (e.g., a compound of Formula III, IV, or V).

In another embodiment, the composition can be comprised of 15-35 weight percent, e.g., 20-30 weight percent, e.g., 24-30 weight percent, e.g., about 26.6 weight percent antipsychotic agent. In one embodiment, the composition can be comprised of 15-35 weight percent, e.g., 20-30 weight percent, e.g., 24-30 weight percent, e.g., about 26.6 weight percent aripiprazole prodrug (e.g., a compound of Formula I or II), or olanzapine prodrug (e.g., a compound of Formula III, IV, or V).

In one embodiment, the pharmaceutical composition is formulated for use in delivering a water-insoluble antipsychotic agent into a host. In a preferred embodiment, the host is human. The composition can be intended for parenteral (e.g., intramuscular, intradermal, or subcutaneous) administration. In certain embodiments, the composition is formulated for delivery through a needle into a host. Accordingly, the composition may be formulated for delivery for injection through a syringe equipped with a needle, where the end-user resuspends the composition prior to use.

In certain embodiments, the pharmaceutical composition comprises a buffer as the aqueous vehicle. The buffer may be selected from a phosphate, citrate, tartrate, or acetate buffer. In a particular embodiment, the buffer is a phosphate buffer.

Also provided herein are methods of making the pharmaceutical compositions described above. The methods involve adding the non-ionic water insoluble and/or immiscible ester co-surfactant to the hydrolytically labile antipsychotic agent to minimize in vitro degradation of the agent during standing. In an embodiment of the method, the non-ionic water insoluble and/or immiscible ester co-surfactant minimizes in vitro degradation of the agent during standing at various temperature and humidity conditions.

Accordingly, in one aspect, provided herein is a method for minimizing in vitro degradation of a hydrolytically labile antipsychotic agent comprising adding to a composition comprising the antipsychotic agent and an aqueous vehicle (a) a non-ionic water insoluble and/or immiscible ester co-surfactant and (b) a water miscible and/or soluble non-ionic surfactant.

In still another aspect, provided herein is a method for the preparation of an aqueous pharmaceutical composition comprising a hydrolytically labile antipsychotic agent, wherein the method comprises adding to a composition comprising the antipsychotic agent and an aqueous vehicle (a) a stabilizing amount of a non-ionic water insoluble and/or immiscible ester co-surfactant and (b) a water miscible and/or soluble non-ionic surfactant. When component (a) is sorbitan laurate, the stabilizing amount can be about 0.2-1 weight percent, about 0.4-0.7 weight percent, or about 0.5 weight percent sorbitan laurate. In an embodiment, the stabilizing amount is not more than 0.5 weight percent sorbitan laurate.

When component (a) is sorbitan laurate, the stabilizing amount also can be about 0.25-0.45 weight percent, about 0.3-0.4 weight percent, or about 0.37 weight percent component (b). In a particular embodiment, the stabilizing amount is about 0.37 weight percent sorbitan laurate.

In embodiments of the method, the resulting formulations are ready to use formulations.

In embodiments of the method, the non-ionic water insoluble and/or immiscible ester co-surfactant is provided in an amount sufficient to minimize in vitro degradation of the antipsychotic agent. In another embodiment, when the ester co-surfactant is sorbitan laurate, about 0.2-1 weight percent, about 0.4-0.7 weight percent, or about 0.5 weight percent sorbitan laurate is an amount sufficient to minimize in vitro degradation of the antipsychotic agent. In other embodiments, the method includes adding not more than 0.5 weight percent sorbitan laurate.

In yet another embodiment, when the ester co-surfactant is sorbitan laurate, 0.25-0.45 weight percent, about 0.3-0.4 weight percent, or about 0.37 weight percent is sufficient to minimize in vitro degradation of the antipsychotic agent. In a particular embodiment, the method includes adding about 0.37 weight percent sorbitan laurate.

In still another embodiment of the methods, the non-ionic water insoluble and/or immiscible ester co-surfactant is provided in an amount providing less than 50 parts per million, e.g., less than 30 parts per million, e.g., less than 10 parts per million, of the hydrolyzed antipsychotic agent degradation products after the total composition stands for at least 24 months.

Also provided herein is a method for treating disorders of the central nervous system, comprising administering an effective amount of any of the preceding compositions to an individual in need of such treatment.

In one embodiment, the disorder is anxiety or depression. In another embodiment, the disorder is bipolar disorder. In still another embodiment, the disorder is autism-related irritability. In yet another embodiment, the disorder is a psychotic condition. The psychotic condition may be schizophrenia or schizophreniform disorder. Alternatively, the psychotic condition may be acute mania.

BRIEF DESCRIPTION OF THE FIGURES

FIG. 3 is a table showing in vitro (standing) studies of the pharmaceutical compositions described herein. This study was conducted at 25° C., with a relative humidity of 60%. The study demonstrated that the total concentration of the prodrug hydrolysis products did not exceed 6 ppm after 12 months of standing or 22 ppm after 24 months of standing.

FIG. 4 is a table showing in vitro (standing) studies of the pharmaceutical compositions described herein. This study was conducted at 40° C., with a relative humidity of 75%. The study demonstrated that the total concentration of the prodrug hydrolysis products did not exceed 16 ppm after 6 months of standing.

FIG. 5 is a table showing in vitro (standing) studies of the pharmaceutical compositions described herein. This study was conducted at 30° C., with a relative humidity of 75%. The study demonstrated that the total concentration of the prodrug hydrolysis products did not exceed 6 ppm after 12 months of standing or 22 ppm after 24 months of standing.

FIG. 6 is a table showing that there are low levels of aldehyde formation in the pharmaceutical compositions described herein. This study was conducted at 40° C., with a relative humidity of 75%.

DETAILED DESCRIPTION OF INVENTION

Pharmaceutical Compositions

Figure 1:
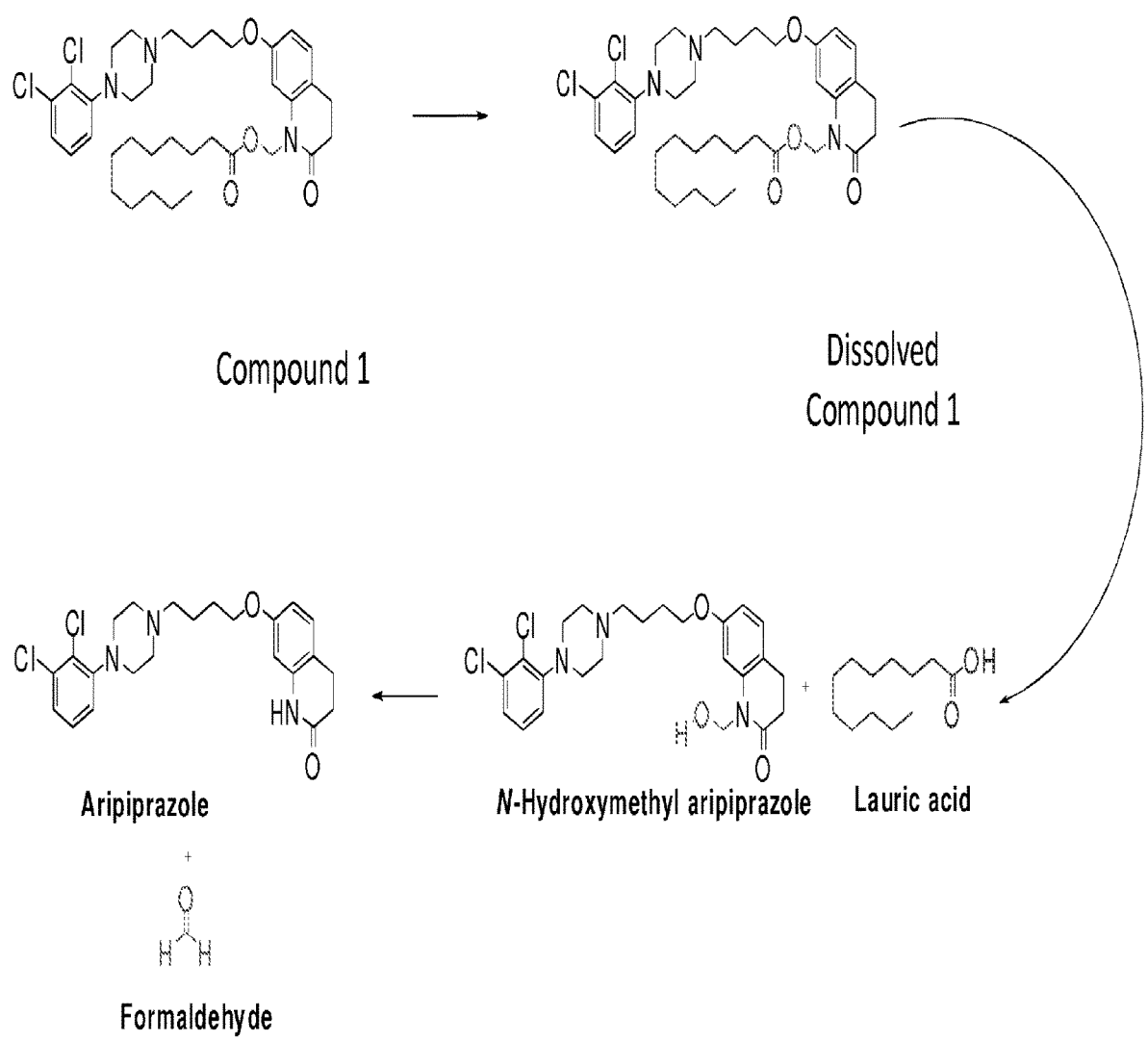
FIG. 1 is a schematic showing in vitro (standing) hydrolysis of a particular aripiprazole prodrug first to an N-hydroxymethyl hydrolysis product and then to aripiprazole. As demonstrated in the exemplification section, the formation of these hydrolysis products is minimized in vitro (i.e., through standing) in the pharmaceutical formulations described herein.

Provided herein are pharmaceutical compositions comprising: (a) a hydrolytically labile antipsychotic agent; (b) a non-ionic water insoluble and/or immiscible ester co-surfactant; (c) a water miscible and/or soluble non-ionic surfactant; and (d) an aqueous vehicle; wherein the pharmaceutical composition comprises a minimal amount of the antipsychotic hydrolysis products after standing for a certain amount of time. For example, the pharmaceutical composition comprises less than 50 parts per million, e.g., less than 30 parts per million, e.g., less than 10 parts per million, of the hydrolyzed antipsychotic agent degradation products after standing for up to, or more than, 24 months. In an embodiment, the pharmaceutical composition comprises less than 50 parts per million, e.g., less than 30 parts per million, e.g., less than 10 parts per million, of the hydrolyzed antipsychotic agent degradation products after standing for at least 1 month, 3 months, 6 months, 9 months, 12 months, 18 months, or 24 months.

In an embodiment, the pharmaceutical composition comprises less than 50 parts per million, e.g., less than 30 parts per million, e.g., less than 20 parts per million, e.g., less than 10 parts per million, e.g., less than 7 parts per million, of the hydrolyzed antipsychotic agent degradation products at certain temperature and humidity conditions, such as 25° C., with a relative humidity of 60%; 40° C., with a relative humidity of 75%; and 30° C., with a relative humidity of 75%. In an embodiment, the pharmaceutical composition comprises less than 50 parts per million, e.g., less than 30 parts per million, e.g., less than 20 parts per million, e.g., less than 10 parts per million, e.g., less than 7 parts per million, of the hydrolyzed antipsychotic agent degradation products at certain temperatures, such as 25° C., 30° C., or 40° C. In an embodiment, the pharmaceutical composition comprises less than 50 parts per million, e.g., less than 30 parts per million, e.g., less than 20 parts per million, e.g., less than 10 parts per million, e.g., less than 7 parts per million, of the hydrolyzed antipsychotic agent degradation products at certain temperatures, such as 25° C.-40° C., over certain time periods, such as at least 1 month, 3 months, 6 months, 9 months, 12 months, 18 months, or 24 months. In an embodiment, the pharmaceutical composition comprises less than 50 parts per million, e.g., less than 30 parts per million, e.g., less than 20 parts per million, e.g., less than 10 parts per million, e.g., less than 7 parts per million, of the hydrolyzed antipsychotic agent degradation products at certain temperatures, such as 25° C.-40° C., over certain time periods, such as 1 month-24 months. In an embodiment, the degradation is minimized at temperatures selected from any of 25° C.-40° C., over a time period selected from any of 1 month-24 months, e.g., at least 1 month, 3 months, 6 months, 9 months, 12 months, 18 months, or 24 months.

In an embodiment, the pharmaceutical composition minimizes formation of the hydrolyzed product when the composition is stored at what the World Health Organization refers to as defines "Normal Storage Conditions" (see WHO Technical Report Series, No. 908, 2003, Annex 9 Guide to Good Storage Practices for Pharmaceuticals, Appendix: Storage and Labeling Conditions): storage in dry, well-ventilated premises at temperatures of 15-25° C. or, depending on climatic conditions, up to 30° C. The compositions provided herein are effective in minimizing drug degradation through, e.g., hydrolysis, in all climactic zones, as well as "Normal Storage Conditions" in those zones as defined by the WHO:

| Climatic Zone | Temperature | Humidity | Minimum Duration |
|---|---|---|---|
| Zone I | 21° C. ± 2° C. | 45% rH ± 5% rH | 12 Months |
| Zone II | 25° C. ± 2° C. | 60% rH ± 5% rH | 12 Months |
| Zone III | 30° C. ± 2° C. | 35% rH ± 5% rH | 12 Months |
| Zone IV | 30° C. ± 2° C. | 65% rH ± 5% rH | 12 Months |
| Zone IVb | 30° C. ± 2° C. | 75% rH ± 5% rH | 12 Months |
| Refrigerated | 5° C. ± 3° C. | No Humidity | 12 Months |
| Frozen | −15° C. ± 5° C. | No Humidity | 12 Months |

Examples of regions in climatic zone 1 are: USA, Japan, UK, Northern Europe, Canada, and Russia.

In an embodiment, the non-ionic water insoluble and/or immiscible ester co-surfactant is a sorbitan ester of a carboxylic acid, wherein the carboxylic acid comprises 4-20 carbon atoms. A preferred sorbitan ester is sorbitan laurate. In another embodiment, the water miscible and/or soluble non-ionic surfactant is a polyoxyethylene derivative of a sorbitan ester of a carboxylic acid, wherein the carboxylic acid comprises 8-14 carbon atoms. A preferred polyoxyethylene derivative is polysorbate 20.

The pharmaceutical compositions provided herein are advantageous because they offer superior preservation of the active agent. In particular, studies have demonstrated that the hydrolytically labile antipsychotic agent undergoes minimal in vitro hydrolysis after sitting (e.g., sitting during storage) for various periods of time (see FIGS. 3-5). This slow degradation was observed even as the solubility of the agent in the injection vehicle composition increased, which was unexpected (see FIG. 2). Without being bound by theory, it is believed that the slow degradation of the therapeutic agent can be attributed to the higher solubility of the compound in the non-ionic water insoluble and/or immiscible ester co-surfactant, e.g., sorbitan laurate, as opposed to the aqueous portion of the vehicle.

In an embodiment, the pharmaceutical composition comprises less than 50 parts per million, less than 30 parts per million, or less than 10 parts per million, of the hydrolyzed antipsychotic agent degradation products after standing for at least 24 months. In an embodiment, the pharmaceutical composition comprises less than 50 parts per million, e.g., less than 30 parts per million, e.g., less than 10 parts per million, of the hydrolyzed antipsychotic agent degradation products after standing for at least 1 month, 3 months, 6 months, 9 months, 12 months, 18 months, or 24 months.

The pharmaceutical composition can further comprise an aqueous vehicle, such as phosphate buffered saline, as well as any of the pharmaceutical components described herein.

The pharmaceutical compositions also offer minimized excipient levels while co-optimizing both re-suspendability and acceptable injectability, and maintain good physiochemical attributes of the antipsychotic agent. The compositions require reduced resuspension times using, for example, hand shaking. In one embodiment, the pharmaceutical compositions can be resuspended for injection within 1-60 seconds of handshaking. Accordingly, the pharmaceutical compositions described herein can also be referred to as "ready to use."

In addition to the re-suspendability and stability advantages described above, the pharmaceutical compositions provided herein result in reduced tissue reactions upon injection.

When the pharmaceutical composition is to be used as an injectable composition, including but not limited to injection through a needle or needle-less injection, it can be formulated into a conventional injectable vehicle. Suitable vehicles include biocompatible and pharmaceutically acceptable solution and/or emulsions.

Provided below are representative drawings of the sorbitan esters that can be used as component (b) in the pharmaceutical compositions described herein. Sorbitan laurate can also be referred to as "sorbitan monolaurate":

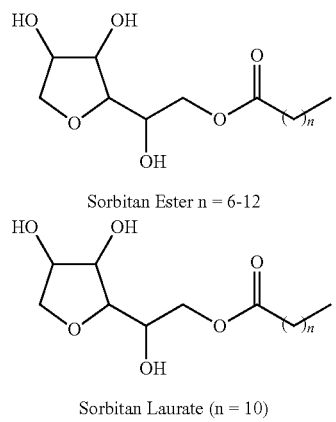

Sorbitan Ester n = 6-12

Sorbitan Laurate (n = 10)

Provided below are representative drawings of the polyoxyethylene derivative of a sorbitan ester of a carboxylic acid used as component (c) in the pharmaceutical compositions:

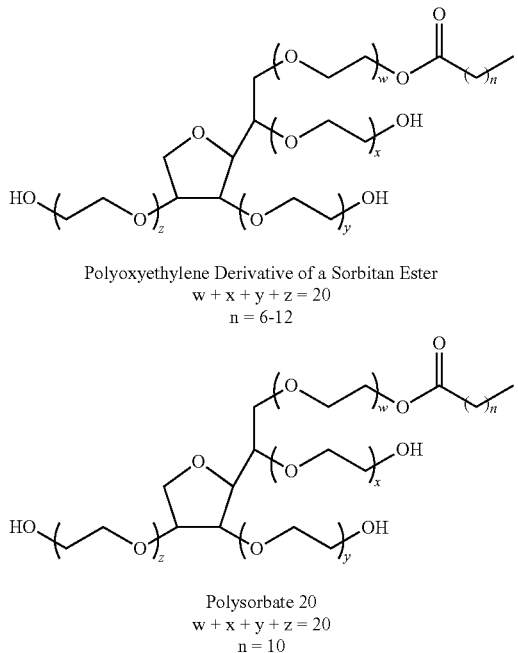

Polyoxyethylene Derivative of a Sorbitan Ester
w + x + y + z = 20
n = 6-12

Polysorbate 20
w + x + y + z = 20
n = 10

In a particular embodiment, component (c) is polysorbate 20, sold under the trademark TWEEN °. The polysorbate can be added in an amount that reduces surface tension of a drug product or aids in suspension stability of the drug product.

The ratios of (b) and (c) can vary. In one embodiment, the ratio of components (b) to (c) is approximately 10 to 0.5, e.g., 10 to 1, e.g., 8 to 1, e.g., 5:2, by weight. In another embodiment, the ratio of components (b) to (c) is approximately 5 to 2, by weight. In still another embodiment, the composition comprises component (a), sorbitan laurate, and polysorbate 20, wherein the ratio of sorbitan laurate and polysorbate 20 is approximately 5 to 2, by weight. In still another embodiment, the composition comprises sorbitan laurate, and polysorbate 20, wherein the ratio of sorbitan laurate and polysorbate 20 is approximately 3 to 1, by weight. In another embodiment, the composition comprises sorbitan laurate, and polysorbate 20, wherein the ratio of sorbitan laurate and polysorbate 20 is approximately 2 to 1, by weight. In yet another embodiment, the composition comprises sorbitan laurate, and polysorbate 20, wherein the ratio of sorbitan laurate and polysorbate 20 is within the range of approximately 3 to 1-2 to 1, by weight. In a particular embodiment, the composition comprises sorbitan laurate, and polysorbate 20, wherein the ratio of sorbitan laurate and polysorbate 20 is approximately a ratio of 3 to a range of 1-2, by weight. In another particular embodiment, the composition comprises sorbitan laurate and polysorbate 20, wherein the ratio of sorbitan laurate and polysorbate 20 is approximately 3 to 1.2, by weight.

As described in the table below, the sorbitan laurate/polysorbate 20 ratio can be approximately 0.625, 1, 1.25, 2, 2.5, or 5, representing a range of 0.625-5:

| SML % | Polysorbate 20% | SML/Polysorbate 20 Ratio |
|---|---|---|
| 1 | 0.8 | 1.25 |
| 0.5 | 0.5 | 1 |
| 0.5 | 0.2 | 2.5 |
| 1 | 0.5 | 2 |
| 0.5 | 0.8 | 0.625 |
| 1 | 0.2 | 5 |
| 0.5 | 0.1 | 5 |

The weight percent of components (b) and (c) can vary in the pharmaceutical compositions provided herein. In one embodiment, the composition comprises about 0.2-1 weight percent component (b), e.g., sorbitan laurate. In another embodiment, the composition comprises about 0.4-0.7 weight percent component (b), e.g., sorbitan laurate. In still another embodiment, the composition comprises about 0.5 weight percent component (b), e.g., sorbitan laurate.

In another embodiment, the composition comprises about 0.25-0.45 weight percent component (b), e.g., sorbitan laurate. In another embodiment, the composition comprises about 0.3-0.4 weight percent component (b), e.g., sorbitan laurate. In still another embodiment, the composition comprises about 0.37 weight percent component (b), e.g., sorbitan laurate.

In another embodiment, the composition comprises about 0.05-0.8 weight percent component (c), e.g., polysorbate 20. In yet another embodiment, the composition comprises about 0.1-0.3 weight percent component (c), e.g., polysorbate 20. In still another embodiment, the composition comprises about 0.2 weight percent polysorbate 20. In yet another embodiment, the composition comprises about 0.15 weight percent polysorbate 20.

The compositions provided herein can also have varying amounts of hydrolytically labile antipsychotic agent. In an embodiment, the antipsychotic agent is an aripiprazole prodrug or an olanzapine prodrug. In a particular embodiment, the antipsychotic agent is an aripiprazole prodrug. In one embodiment, the composition comprises approximately 15-35 weight percent aripiprazole prodrug (e.g., a compound of Formula I or II), or olanzapine prodrug (e.g., a compound of Formula III, IV, or V). In another embodiment, the composition comprises approximately 20-30 weight percent aripiprazole prodrug (e.g., a compound of Formula I or II), or olanzapine prodrug (e.g., a compound of Formula III, IV, or V). In still another embodiment, the composition comprises approximately 20-26 weight percent aripiprazole prodrug (e.g., a compound of Formula I or II), or olanzapine prodrug (e.g., a compound of Formula III, IV, or V). In another embodiment, the composition comprises approximately 24-26 weight percent aripiprazole prodrug (e.g., a compound of Formula I or II), or olanzapine prodrug (e.g., a compound of Formula III, IV, or V).

In one embodiment, the composition comprises approximately 15-35 weight percent aripiprazole prodrug (e.g., a compound of Formula I or II), or olanzapine prodrug (e.g., a compound of Formula III, IV, or V). In another embodiment, the composition comprises approximately 20-30 weight percent aripiprazole prodrug (e.g., a compound of Formula I or II), or olanzapine prodrug (e.g., a compound of Formula III, IV, or V). In still another embodiment, the composition comprises approximately 24-30 weight percent aripiprazole prodrug (e.g., a compound of Formula I or II), or olanzapine prodrug (e.g., a compound of Formula III, IV, or V). In a particular embodiment, the composition comprises approximately 26.6 weight percent aripiprazole prodrug (e.g., a compound of Formula I or II), or olanzapine prodrug (e.g., a compound of Formula III, IV, or V).

In an embodiment, the pharmaceutical composition comprises:
(a) 15-35 weight percent aripiprazole prodrug (e.g., a compound of Formula I or II) or olanzapine prodrug (e.g., a compound of Formula III, IV, or V);
(b) 0.25-0.45 weight percent sorbitan laurate;
(c) 0.2-1 weight percent polysorbate 20; and
(d) an aqueous vehicle.

In another embodiment, the pharmaceutical composition comprises:
(a) 24-30 weight percent aripiprazole prodrug (e.g., a compound of Formula I or II) or olanzapine prodrug (e.g., a compound of Formula III, IV, or V);
(b) 0.3-0.4 weight percent sorbitan laurate;
(c) 0.1-0.3 weight percent polysorbate 20; and
(d) an aqueous vehicle.

In still another embodiment, the pharmaceutical composition comprises:
(a) about 26.6 weight percent aripiprazole prodrug (e.g., a compound of Formula I or II) or olanzapine prodrug (e.g., a compound of Formula III, IV, or V);
(b) about 0.37 weight percent sorbitan laurate;
(c) about 0.15 weight percent polysorbate 20; and
(d) an aqueous vehicle.

In an embodiment, the pharmaceutical composition comprises:
(a) 15-35 weight percent compound I:

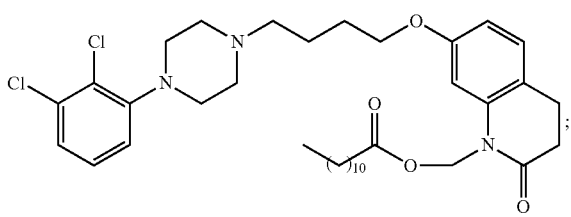

(b) 0.25-0.45 weight percent sorbitan laurate;
(c) 0.2-1 weight percent polysorbate 20; and
(d) an aqueous vehicle.

In another embodiment, the pharmaceutical composition comprises:
(a) 24-30 weight percent compound I:

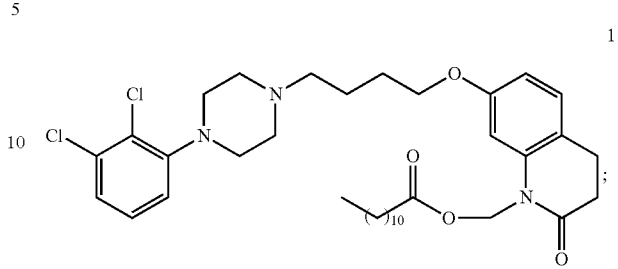

(b) 0.3-0.4 weight percent sorbitan laurate;
(c) 0.1-0.3 weight percent polysorbate 20; and
(d) an aqueous vehicle.

In still another embodiment, the pharmaceutical composition comprises:
(a) about 26.6 weight percent compound I:

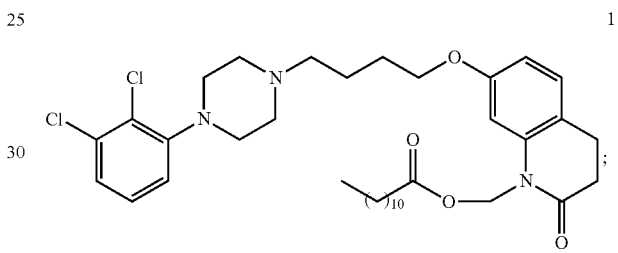

(b) about 0.37 weight percent sorbitan laurate;
(c) about 0.15 weight percent polysorbate 20; and
(d) an aqueous vehicle.

In one embodiment, the pharmaceutical has a high storage stability such that the decomposition of a hydrolytically labile antipsychotic prodrug (e.g., aripiprazole prodrug, e.g., compound I) to its antipsychotic hydrolysis products will be less than 5 ppm when the composition is stored at 25° C. and 60% relative humidity for 6 months. In one embodiment, the decomposition of aripiprazole prodrug (e.g., compound I) to N-hydroxymethyl hydrolysis products will be less than 5 ppm when the composition is stored at 25° C. and 60% relative humidity for 6 months.

In another embodiment, the decomposition of the hydrolytically labile antipsychotic prodrug (e.g., aripiprazole prodrug, e.g., compound I) to its antipsychotic hydrolysis products will not exceed 6 ppm when the composition is stored at 25° C. and 60% relative humidity for 9 months. In one embodiment, the decomposition of aripiprazole prodrug (e.g., compound I) to N-hydroxymethyl hydrolysis products will not exceed 6 ppm when the composition is stored at 25° C. and 60% relative humidity for 9 months.

In another embodiment, the decomposition of the hydrolytically labile antipsychotic prodrug (e.g., aripiprazole prodrug, e.g., compound I) to its antipsychotic hydrolysis products will not exceed 14 ppm when the composition is stored at 25° C. and 60% relative humidity for 18 months. In one embodiment, the decomposition of aripiprazole prodrug (e.g., compound I) to N-hydroxymethyl hydrolysis products will not exceed 14 ppm when the composition is stored at 25° C. and 60% relative humidity for 18 months.

In still another embodiment, the decomposition of the hydrolytically labile a antipsychotic prodrug (e.g., aripiprazole prodrug, e.g., compound I) to its antipsychotic hydrolysis products will not exceed 24 ppm when the composition is stored at 25° C. and 60% relative humidity for 24 months. In one embodiment, the decomposition of aripiprazole prodrug (e.g., compound I) to N-hydroxymethyl hydrolysis products will not exceed 24 ppm when the composition is stored at 25° C. and 60% relative humidity for 24 months.

In another embodiment, the pharmaceutical has a high storage stability such that the decomposition of the hydrolytically labile antipsychotic prodrug (e.g., aripiprazole prodrug, e.g., compound I) to its antipsychotic hydrolysis products will be less than 5 ppm when the composition is stored at 30° C. and 75% relative humidity for 6 months. In one embodiment, the decomposition of aripiprazole prodrug (e.g., compound I) to N-hydroxymethyl hydrolysis products will be less than 5 ppm when the composition is stored at 25° C. and 60% relative humidity for 6 months.

In yet another embodiment, the decomposition of hydrolytically labile antipsychotic prodrug (e.g., aripiprazole prodrug, e.g., compound I) to its antipsychotic hydrolysis products will not exceed 6 ppm when the composition is stored at 30° C. and 75% relative humidity for 12 months. In one embodiment, the decomposition of aripiprazole prodrug (e.g., compound I) to N-hydroxymethyl hydrolysis products will not exceed 6 ppm when the composition is stored at 30° C. and 75% relative humidity for 12 months.

In still another embodiment, the decomposition of hydrolytically labile antipsychotic prodrug (e.g., aripiprazole prodrug, e.g., compound I) to its antipsychotic hydrolysis products will not exceed 24 ppm when the composition is stored at 30° C. and 75% relative humidity for 24 months. In one embodiment, the decomposition of aripiprazole prodrug (e.g., compound I) to N-hydroxymethyl hydrolysis products will not exceed 24 ppm when the composition is stored at 30° C. and 75% relative humidity for 24 months.

In yet another embodiment, the pharmaceutical has a high storage stability such that the decomposition of a hydrolytically labile antipsychotic prodrug (e.g., aripiprazole prodrug, e.g., compound I) to its antipsychotic hydrolysis products will be less than 5 ppm when the composition is stored at 40° C. and 75% relative humidity for 3 months. In one embodiment, the decomposition of aripiprazole prodrug (e.g., compound I) to N-hydroxymethyl hydrolysis products will be less than 5 ppm when the composition is stored at 40° C. and 75% relative humidity for 3 months.

In another embodiment, the decomposition of the hydrolytically labile antipsychotic prodrug (e.g., aripiprazole prodrug, e.g., compound I) to its antipsychotic hydrolysis products will not exceed 16 ppm when the composition is stored at 40° C. and 75% relative humidity for 12 months. In one embodiment, the decomposition of aripiprazole prodrug (e.g., compound I) to N-hydroxymethyl hydrolysis products will not exceed 16 ppm when the composition is stored at 40° C. and 75% relative humidity for 12 months.

In certain embodiments, the composition is stored in a sealed (e.g., septum stoppered), colorless, glass vial.

The aqueous vehicle of the pharmaceutical compositions provided herein can be a buffer. The buffer may be selected from a phosphate, citrate, tartrate or acetate buffer. In a particular embodiment, the buffer is a phosphate buffer.

The pharmaceutical compositions provided herein can further comprise additional components. For example, the use of additional wetting agents or surfactants in a pharmaceutical composition may promote one or more of the following:

(1) Surface tension reduction, which may aid in wetting, since a 'lower surface tension' liquid will wet surfaces or particles more readily than a 'high surface tension' liquid. Lowering the surface tension of a liquid may also decrease the incidence of foaming. The surface tension of a liquid will be lower as more surfactant is added;

(2) Formation of micelles (i.e., spherical or non-spherical surfactant structures in solution that have the capability to dissolve non-soluble components); and/or (3) Increase of suspension physical stability.

The pharmaceutical compositions can also contain an aqueous vehicle, which is a vehicle that dilutes and suspends the drug. The vehicle of interest herein is one that is pharmaceutically acceptable (safe and non-toxic for administration to a human) and is useful for the preparation of a reconstituted formulation. Exemplary vehicles include sterile water, sterile water for injection (WFI), bacteriostatic water for injection (BWFI), a pH buffered solution (e.g., phosphate-buffered saline), sterile saline solution, Ringer's solution, or dextrose solution. The buffer can be phosphate, citrate, tartrate, or acetate. In a particular embodiment, the vehicle is phosphate-buffered saline, which is a water-based salt solution containing either sodium chloride or potassium chloride and either sodium phosphate or potassium phosphate. In one embodiment, the phosphate buffer comprises isotonic saline with 5-50 mM phosphate buffer at pH 4.0-9.0, e.g., 5.0-8.0, e.g., 5.0-7.5.

The pharmaceutical compositions can further contain an additional surfactant that preferentially adsorbs to an interface between two immiscible phases, such as the interface between water and an organic polymer solution, a water/air interface or organic solvent/air interface. Suitable surfactants include but are not limited to fatty alcohols such as polyethylene glycols (PEGs) and cetyl alcohol.

Optionally, the pharmaceutical compositions can further comprise a dispersant, such as, for example, carboxymethyl cellulose (CMC), carboxymethyl cellulose sodium, cross-linked sodium carboxymethyl cellulose, calcium carboxymethyl cellulose, and low substituted hydroxypropyl cellulose magnesium aluminum silicate, or a mixture thereof. In a particular embodiment, the pharmaceutical composition comprises carboxymethyl cellulose.

The pharmaceutical compositions may also optionally comprise an antioxidant to inhibit the oxidation of ingredients. Some examples of antioxidants include, but are not limited to, ascorbic acid, ascorbyl palmitate, butylated hydroxyanisole, a mixture of 2- and 3-tertiary-butyl-4-hydroxyanisole, butylated hydroxytoluene, sodium iso-ascorbate, dihydroguaretic acid, potassium sorbate, sodium bisulfate, sodium metabisulfate, sorbic acid, potassium ascorbate, vitamin E, 4-chloro-2,6-ditertiary butylphenol, alpha-tocopherol, and propylgallate.

The pharmaceutical compositions can further include a lipid, e.g., a neutral lipid. Neutral lipids include any lipid that remains neutrally charged at a pH between about 4 and 9. Neutral lipids include, without limitation, cholesterol, other sterols and derivatives thereof, phospholipids, and combinations thereof. The phospholipids include any one phospholipid or combination of phospholipids capable of forming liposomes.

They include phosphatidylcholines, phosphatidylethanolamines, lecithin and fractions thereof, phosphatidic acid, phosphatidylglycerols, phosphatidylinositols, phosphatidylserines, plasmalogens and sphingomyelins. The phosphatidylcholines include, without limitation, those obtained from egg, soy beans, or other plant sources or those that are partially or wholly synthetic or of variable lipid chain length and unsaturation, POPC, OPPC, natural or hydrogenated soy bean PC, natural or hydrogenated egg PC, DMPC, DPPC, DSPC, DOPC, and derivatives thereof. In one embodiment, phosphatidylcholines are POPC, non-hydrogenated soy bean PC and non-hydrogenated egg PC. Phosphatidylethanolamines include, without limitation, DOPE, DMPE and DPPE and derivatives thereof. Phosphatidylglycerols include, without limitation, DMPG, DLPG, DPPG, and DSPG. Phosphatidic acids include, without limitation, DSPA, DMPA, DLPA, and DPPA.

The pharmaceutical compositions can also advantageously employ a density enhancing agent, such as a sugar, e.g., mannitol or sorbitol, and/or a tonicity adjusting agent, such as sodium chloride or glycerol.

Other pharmaceutical carriers that could be used in the pharmaceutical compositions provided herein also include water, aqueous methylcellulose solutions, saline, dextrose solutions, fructose solutions, ethanol, or oils of animal, vegetative, or synthetic origin. The pharmaceutical carrier may also contain preservatives, and buffers as are known in the art.

The terms "pharmaceutical composition", "formulation", "injectable composition," etc. are used synonymously throughout the application.

The pharmaceutical compositions described herein may also be in the form of an emulsion. The term "emulsion" as used in this specification denotes a two-phase system in which one phase is finely dispersed in the other phase. An emulsifier can be used in the pharmaceutical compositions to form the emulsion. The term emulsifier, as used by this invention, denotes an agent that can reduce and/or eliminate the surface and the interfacial tension in a two-phase system. Such an agent possesses both hydrophilic and lipophilic groups in the emulsifier agent.

The pharmaceutical compositions described herein may also be in the form of adispersion. As used herein, the term "dispersion" is to be understood as a mixture in which fine particles of one substance (e.g., a drug) are scattered throughout another substance (e.g., a liquid). Dispersions include suspensions and colloids.

The methods of the invention include administering the compositions described herein, thereby obtaining an extended release or sustained release profile in the patient. "Extended-release" or "sustained-release" includes dosage forms whose drug-release characteristics of time course and/or location are chosen to accomplish therapeutic or convenience objectives not offered by conventional dosage forms such as a solution or an immediate release dosage form. An extended release profile includes deliveries that achieve a therapeutically effective amount of the antipsychotic agent, e.g., aripiprazole prodrug (e.g., a compound of Formula I or II), or olanzapine prodrug (e.g., a compound of Formula III, IV or V), is present in the plasma of the individual for at least about 7 days, preferably at least about 14 days, or more preferably at least about 21 days alternatively for at least 2, 3, 4, 6 or 8 weeks or as much as three months.

In one embodiment, the pharmaceutical compositions can be administered as a single or sole (undivided) dose. However, the composition is also useful for those individuals that require constant or chronic therapy, such as those that receive repeated doses over several hours, days, weeks, months, or more. In such dosing regimens, the method can comprise a first administration of a first extended release composition and a second administration of a second extended release composition. The second composition can be the same, substantially the same or different as the first and can include the same active agent or a different active agent. For example, the second composition can be administered at about 7 days, or more, such as at least about 14 days, or at least about 17 days, after the first administration, where the first administration results in the release of agent for a period of 1, 2, 3, 4, 5, 6, 7, 8, 9, 10, 11, 12, 13, 14 days, or more.

The injectable, pharmaceutical compositions described herein can be injected into a patient in any number of ways. The term "injectable" as used herein refers to a composition that is suitable to be delivered to an individual in an injection, such as with an injection device, including one that employs a syringe or a cartridge, which may be housed in a manual injection device or an auto-injection device, for example. Specifically, the injectable composition is suitable for parenteral administration. As used herein, the term "parenteral administration" refers to administration through injection or infusion. Parenteral administration includes, but is not limited to, intravenous administration, intradermal administration, subcutaneous administration or intramuscular administration. The term "intravenous administration" means administration into a vein. "Intradermal administration" is injection into the upper layer of skin (i.e., the dermis), just beneath the epidermis. "Subcutaneous administration" refers to administration just below the skin. "Intramuscular administration" is the injection directly into a muscle.

Antipsychotic Agents

As discussed above, the pharmaceutical compositions provided herein are useful for the administration of hydrolytically labile antipsychotic agents to a subject. In particular, the pharmaceutical compositions minimize the formation of the hydrolysis product of the hydrolytically labile antipsychotic agent contained therein during standing, such that the pharmaceutical composition has an improved shelf life. As used herein the term "antipsychotic" refers all drugs used to treat psychosis. Common conditions for which antipsychotics are prescribed include schizophrenia, mania, and delusional disorder, although antipsychotics are also used to counter psychosis associated with a wide range of other diagnoses. Antipsychotics also act as mood stabilizers making them suitable for the treatment of bipolar disorder (even when no symptoms of psychosis are present). The pharmaceutical compositions provided herein are particularly useful for formulating a water-insoluble antipsychotic into an injectable composition.

In one embodiment, the antipsychotic drug of the pharmaceutical composition is an aripiprazole prodrug. The aripiprazole prodrug can comprise, consist essentially of, or consist of an aripiprazole prodrug in a crystalline, non-crystalline or amorphous form, an aripiprazole prodrug solvate (including ethanolates and hydrates), or other aripiprazole prodrug polymorphs.

The term "prodrug" is art-recognized and is intended to encompass compounds which, under physiological conditions, are converted into active compounds, e.g., those described herein. A common method for making a prodrug is to select moieties that are hydrolyzed or otherwise cleaved under physiological conditions to provide the desired compound. In other embodiments, the prodrug is converted by an enzymatic activity of the host animal.

Preferred aripiprazole prodrugs that can be used in the pharmaceutical compositions include the prodrugs described in U.S. Publication No. 2011/0003828, which is incorporated herein by reference in its entirety.

In a particular embodiment, the aripiprazole prodrug is a compound of Formula (I) or Formula (II):

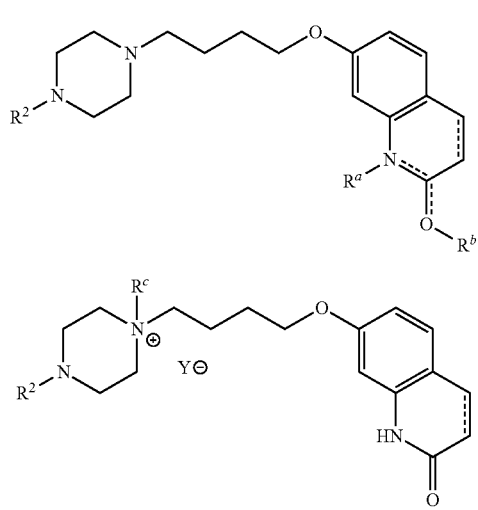

wherein
R$^a$ is absent, and R$^b$ is —CH$_2$OC(O)R$^1$, —CH$_2$OC(O)OR$^1$, —CH$_2$OC(O)N(R$^1$)$_2$ or —C(O)R$^1$;
or
R$^b$ is absent, and R$^a$ is —CH$_2$OC(O)R$^1$, —CH$_2$OC(O)OR$^1$, —CH$_2$OC(O)N(R$^1$)$_2$ or —C(O)R$^1$;
R$^c$ is —CH$_2$OC(O)R$^1$, —CH$_2$OC(O)OR$^1$, —CH$_2$OC(O)N(R$^1$)$_2$ or —C(O)R$^1$;
wherein each R$^1$ is independently selected from the group consisting of hydrogen, substituted or unsubstituted aliphatic, and substituted or unsubstituted aryl; and
wherein each R$^2$ is selected from the group consisting of substituted or unsubstituted aryl and substituted or unsubstituted heteroaryl;
wherein Y$^\ominus$ is a pharmaceutically acceptable counterion; and
wherein ===== represents a single or double bond.

Suitable counterions include, e.g., chloride, bromide, iodide, sulfate, phosphate, acetate, benzoate, tartrate, citrate, propionate, gluconate, lactate, maleate, fumarate, camsylate, glucepate, mesylate, napsylate, pamoate, conjugate bases of organic carboxylic acids, and the like.

In one embodiment of formula (I), the aripiprazole prodrug is a compound of formula (I'):

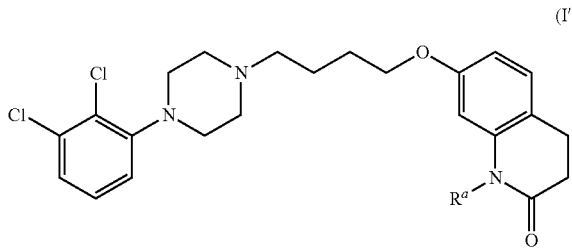

wherein R$^a$ is CH$_2$OC(O)R$^1$ and wherein R$^1$ is selected from substituted or unsubstituted aliphatic.

In a particular embodiment of formula (I'), R$^1$ is —CH$_2$OC(O)—(CH$_2$)$_4$CH$_3$ (Compound A). In another particular embodiment of formula (I'), R$^1$ is —CH$_2$OC(O)—(CH$_2$)$_{10}$H$_3$ (Compound 1). Compounds A and 1 are depicted below:

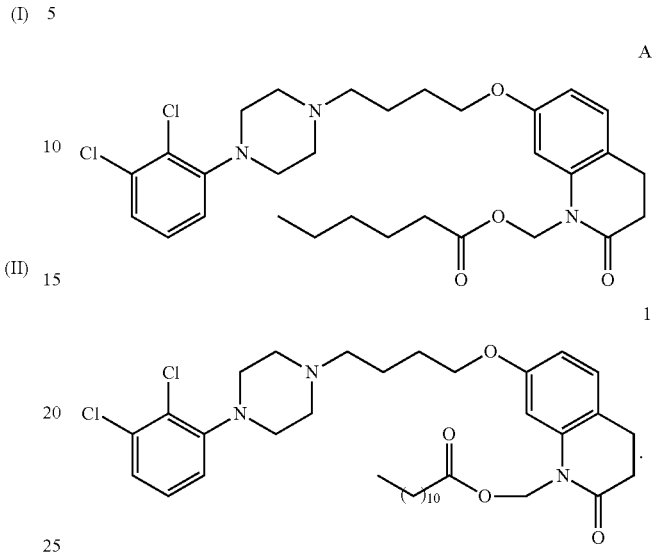

In an embodiment of the pharmaceutical composition, when the hydrolytically labile antipsychotic agent is an aripiprazole prodrug, the hydrolyzed drug product that is formed to only a minimal extent can be the aripiprazole drug form:

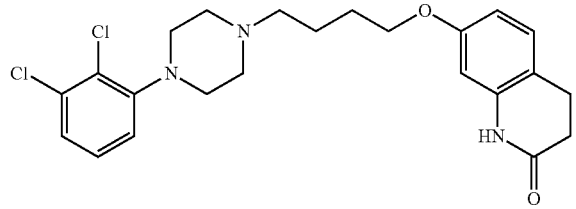 [SMILES: O=C1CCc2ccc(OCCCCN3CCN(c4cccc(Cl)c4Cl)CC3)cc2N1]

and/or the N-methylene hydroxy compound having the following formula:

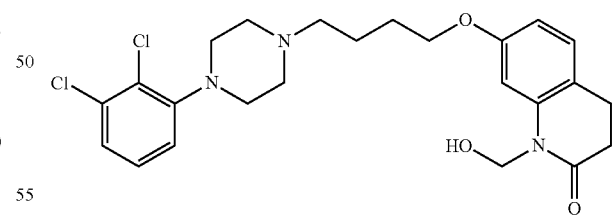

In another embodiment, the antipsychotic drug of the pharmaceutical composition is an olanzapine prodrug. The olanzapine prodrug substance can comprise, consist essentially of, or consist of the olanzapine prodrug in a crystalline, non-crystalline or amorphous form, an olanzapine prodrug solvate (including for example ethanolates and hydrates), or other olanzapine prodrug polymorphs.

The olanzapine drug substance can also include olanzapine prodrugs of Formula (III), (IV) or (V):

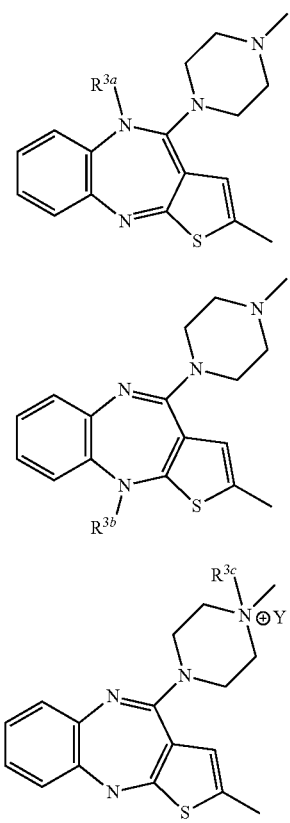

(III)

(IV)

(V)

wherein $R^{3a}$, $R^{3b}$, and $R^{ac}$ are independently —CH$_2$OC(O)R$^1$, —CH$_2$OC(O)OR$^1$, —CH$_2$OC(O)N(R$^1$)$_2$, —C(O)R' or —C(O)OC(R$^4$)(R$^5$)—OC(O)(G$^{12}$)$_m$R$^6$;

wherein R$^1$ is independently selected from the group consisting of hydrogen, substituted or unsubstituted aliphatic, and substituted or unsubstituted aryl;

wherein each R$^4$ and R$^5$ is independently selected from hydrogen, C$_1$-C$_3$ alkyl, aryl or substituted aryl; preferably, hydrogen or methyl;

wherein G$^{12}$ is selected from NH, CH$_2$, —S— or —O—;

wherein m is 0 or 1;

wherein R$^6$ is selected from C$_{13}$-C$_{26}$-alkyl, substituted C$_{13}$-C$_{26}$-alkyl, C$_{13}$-C$_{26}$-alkenyl, substituted C$_{13}$-C$_{26}$-alkenyl, C$_{13}$-C$_{26}$-alkynyl, substituted C$_{13}$-C$_{26}$-alkynyl, C$_{13}$-C$_{26}$-cycloalkyl, and substituted C$_{13}$-C$_{26}$-cycloalkyl, aryl-C$_{13}$-C$_{26}$-alkyl, substituted aryl-C$_{13}$-C$_{26}$-alkyl, C$_1$-C$_{10}$-aryl, substituted C$_1$-C$_{10}$-aryl, heteroaryl-C$_{13}$-C$_{26}$-alkyl, substituted heteroaryl-C$_{13}$-C$_{26}$-alkyl; optionally substituted C$_{13}$-C$_{26}$-alkylaryl, optionally substituted C$_{13}$-C$_{26}$-alkenylaryl and optionally substituted C$_{13}$-C$_{26}$-alkynylaryl; and wherein Y$^\ominus$ is a pharmaceutically acceptable counterion.

Suitable counterions include, e.g., chloride, bromide, iodide, sulfate, phosphate, acetate, benzoate, tartrate, citrate, propionate, gluconate, lactate, maleate, fumarate, camsylate, glucepate, mesylate, napsylate, pamoate, conjugate bases of organic carboxylic acids, and the like.

In one embodiment of formula (III), R$^{3a}$ is —C(O)OCH$_2$OC(O)R$^6$ and R$^6$ is selected from C$_{13}$-C$_{26}$-alkyl. In a particular embodiment of formula (III), R$^{3a}$ is —C(O)OCH$_2$OC(O)(CH$_2$)$_{14}$CH$_3$ (Compound O-56). In another particular embodiment of formula (III), R$^{3a}$ is —C(O)OCH$_2$OC(O)(CH$_2$)$_{16}$CH$_3$ (Compound O-111). In still another particular embodiment of formula (III), R$^{3a}$ is —C(O)OCH$_2$OC(O)(CH$_2$)$_{18}$CH$_3$ (Compound O-112). Compounds O-56, O-111 and O-112 are depicted below:

O-56

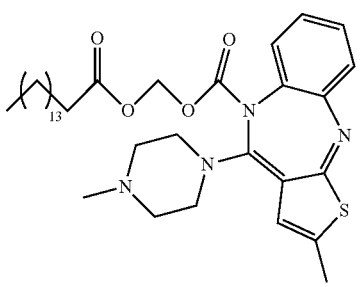

O-111

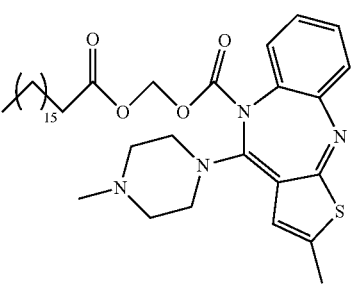

O-112

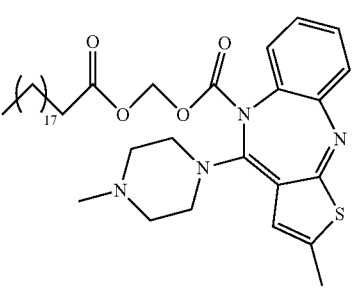

In one embodiment of formula (IV), R$^{3b}$ is —C(O)OCH$_2$OC(O)R$^6$ and R$^6$ is selected from C$_{13}$-C$_{26}$-alkyl. In a particular embodiment of formula (IV), R$^{3b}$ is —C(O)OCH$_2$OC(O)(CH$_2$)$_{14}$CH$_3$ (Compound O-7). In another particular embodiment of formula (IV), R$^{3b}$ is —C(O)OCH$_2$OC(O)(CH$_2$)$_{16}$CH$_3$ (Compound O-8). In still another particular embodiment of formula (IV), R$^{3b}$ is —C(O)OCH$_2$OC(O)(CH$_2$)$_{18}$CH$_3$ (Compound O-9). Compounds O-7, O-8 and O-9 are depicted below:

O-7

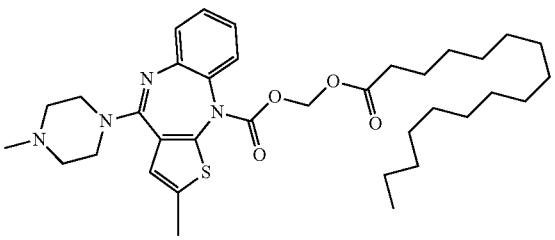

-continued

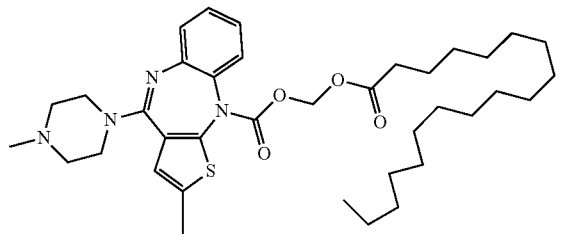

O-8

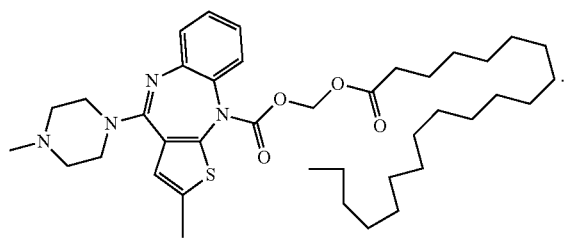

O-9

Accordingly, aripiprazole, or olanzapine, or a compound of Formula I, II, III, IV, or V can be referred to as an "antipsychosis agent" or "hydrolytically labile antipsychotic agent."

An "aliphatic group" or "aliphatic" is non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms, and may be substituted or unsubstituted.

An aliphatic group, when used as a linker, preferably contains between about 1 and about 24 atoms, more preferably between about 4 to about 24 atoms, more preferably between about 4 to about 12 atoms, more typically between about 4 and about 8 atoms. An aliphatic group, when used as a substituent, preferably contains between about 1 and about 30 atoms, more preferably between about 4 to about 19 atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl groups described herein.

In certain embodiments, the aliphatic groups of the present invention are alkyl chains containing from 5 to 11 carbon atoms. In other embodiments, the aliphatic groups are alkyl chains containing from 15 to 19 carbon atoms.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane, and biphenyl. In an embodiment, aryl is unsubstituted or independently substituted one or more times with halogen, $C_{1-6}$ alkyl, or O—$C_{1-6}$ alkyl.

The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, amino alkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The term "compound" is defined herein to include pharmaceutically acceptable salts, solvates, hydrates, polymorphs, enantiomers, diastereoisomers, racemates and the like of the compounds having a formula as set forth herein.

Methods of Treatment

The pharmaceutical compositions provided herein can be used for treatment of a variety of disorders in a subject in need thereof. For example, the disclosed compositions may be used to treat conditions selected from: disorders such as cerebral deficit subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, cerebral deficits secondary to prolonged status epilepticus, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, social phobia, obsessive compulsive disorder, and post-traumatic stress disorder (PTSD)), attention deficit disorder (ADD), attention deficit hyperactivity disorder (ADHD), mood disorders (including depression, mania, bipolar disorders), circadian rhythm disorders (including jet lag and shift work), trigeminal neuralgia, hearing loss, tinnitus, macular degeneration of the eye, emesis, brain edema, pain (including acute and chronic pain states, severe pain, intractable pain, neuropathic pain, inflammatory pain, and post-traumatic pain), tardive dyskinesia, sleep disorders (including narcolepsy), attention deficit/hyperactivity disorder, and conduct disorder.

In another embodiment, the present invention provides a method of treating cardiac and cardiovascular disorders such as angina, arrhythmia, and hypertension, in a patient in need thereof. The method comprises administering to the subject a therapeutically effective amount of a composition of the invention or a pharmaceutically acceptable salt thereof.

The invention further relates to the treatment of fever, diabetes, allergy, asthma, infection, inflammation, and ulcers in a patient in need thereof, comprising administering to the subject a therapeutically effective amount of a composition of the invention or a pharmaceutically acceptable salt thereof.

The invention further relates to the treatment of sleep modulation comprising administration of a composition of the invention. Sleep modulation includes decreasing the time to sleep onset, increasing the average sleep bout length, and increasing the maximum sleep bout length.

In a particular embodiment, the pharmaceutical compositions described herein can be used to treat anxiety, depression, bipolar disorder, autism-related irritability, and psychotic conditions including acute mania, schizophrenia, and schizophreniform disorder in a subject.

The term "treated," "treating" or "treatment" includes the diminishment or alleviation of at least one symptom associated with psychosis or a related CNS disorder. The term "treated," "treating" or "treatment" as used in reference to a disease or condition shall mean to intervene in such disease or condition so as to prevent or slow the development of, prevent or slow the progression of, halt the progression of, or eliminate the disease or condition.

As used herein, the term "modulating" or "modulate" refers to an effect of altering a biological activity, especially a biological activity associated with an injection site reaction.

The term "subject" is intended to include animals, which are capable of suffering from or afflicted with dementia associated with psychosis or a related CNS disorder, including, without limitation, psychotic conditions including acute mania, schizophrenia and schizophreniform disorder, bipolar disorder, anxiety and depression. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from any of the diseases described herein.

The term "about" or "approximately" usually means within 20%, more preferably within 10%, and most preferably still within 5% of a given value or range. Alternatively, especially in biological systems, the term "about" means within about a log (i.e., an order of magnitude), preferably within a factor of two of a given value.

In one embodiment, a therapeutically effective amount of the agent is given to a subject using the pharmaceutical compositions provided herein. The term "therapeutically effective amount" is further meant to define an amount resulting in the improvement of any parameters or clinical symptoms. The actual dose may vary with each patient and does not necessarily indicate a total elimination of all disease symptoms. In the case of antipsychotics, the management of exacerbations and maintenance of remission of psychiatric symptoms are main goals of therapy, and selection of the appropriate drug and dosage in a particular disease balances these goals with the minimization of adverse events attributable to the drug.

A therapeutically effective amount of the compound used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

Preferred suitable dosages for the compounds used in the treatment described herein are on the order of about 1 mg to about 600 mg, preferably about 3, 5, 10, 15, 20, 25, 30, 35, 40, 45, 50, 55, 60, 65, 70, 75, 80, 90, 95, 100, 120, 140, 160, 180, 200, 220, 240, 260, 280, 300, 320, 340, 360, 380, 400, 420, 440, 460, 480, 500, 520, 540, 560, 580 to about 600 mgs total of active agent. Dosing schedules may be adjusted to provide the optimal therapeutic response. For example, administration can be one to three times daily for a time course of one day to several days, weeks, months, and even years, and may even be for the life of the patient. Practically speaking, a unit dose of any given composition used in the treatment described herein can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth. Unit dose preparations provided herein can contain aripiprazole, a compound of Formula I or a compound of Formula II in the range of about 20 to about 900, e.g., 60 to about 800, mgs (aripiprazole base equivalents). Unit dose preparations provided herein can contain olanzapine, a compound of Formula III, or a compound of Formula IV in the range of 40 to about 500 mgs (olanzapine base equivalents). Unit dose preparations provided herein can contain a compound of Formula V in the range of 160 to about 1000 mgs (lurasidone base equivalents).

Preferred amounts according to the selected mode of administration are able to be determined by one skilled in the art. Pharmaceutical compositions can be manufactured utilizing techniques known in the art. Typically the therapeutically effective amount of the compound will be admixed with a pharmaceutically acceptable carrier.

EXEMPLIFICATION OF THE INVENTION

The invention is further illustrated by the following examples. The examples should not be construed as further limiting.

Example I—Stability Study

FIG. 1 shows in vitro hydrolysis of a particular aripiprazole prodrug to N-methyl-hydroxy hydrolysis products. As demonstrated below, the formation of these hydrolysis products is minimized in vitro (i.e., through standing) in the pharmaceutical formulations described herein.

Figure 2:
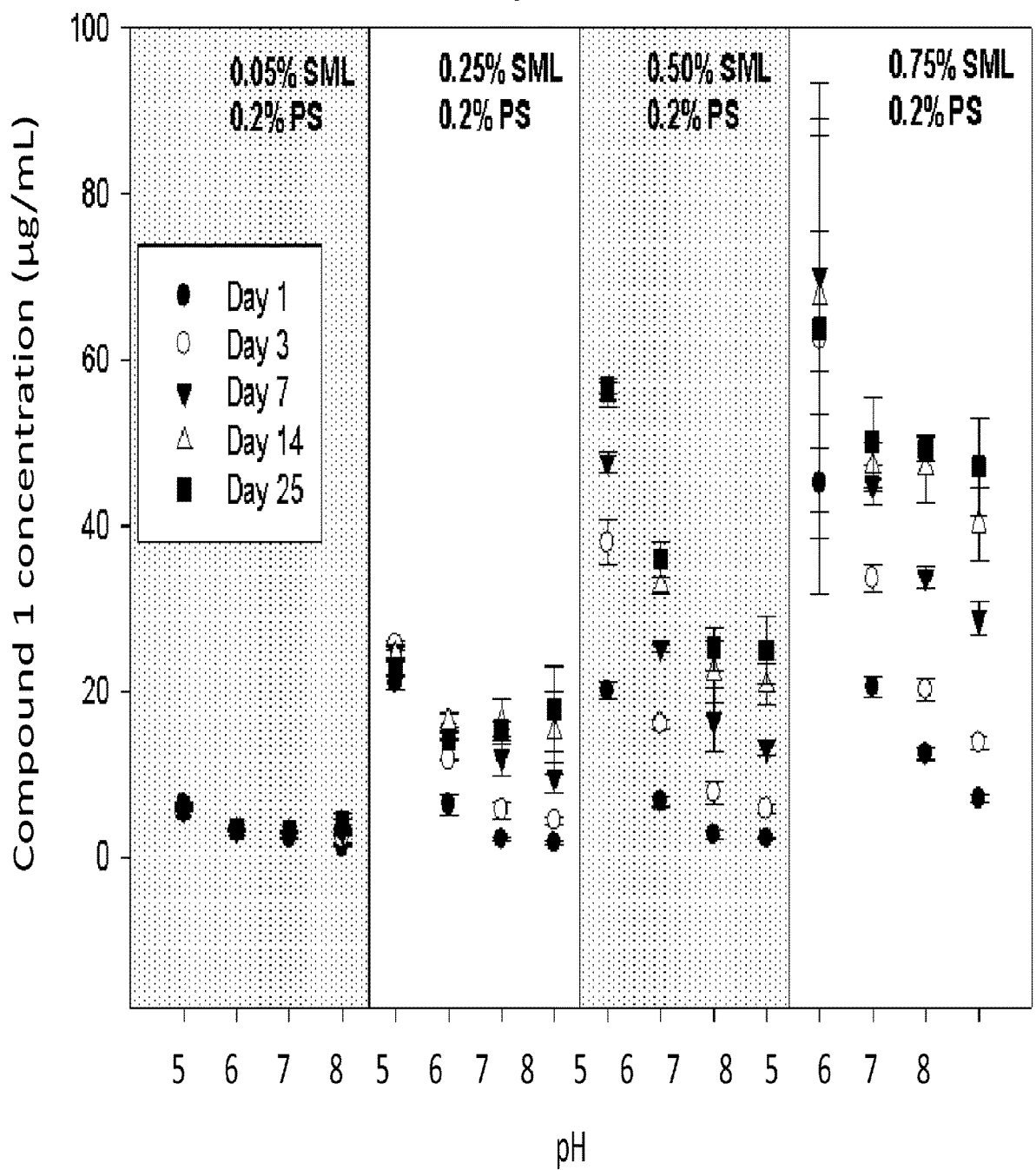
FIG. 2 is a graph showing the increased solubility of Compound 1 with increasing concentration of a non-ionic water insoluble and/or immiscible ester co-surfactant. The experiments demonstrate that the total concentration of the prodrug hydrolysis products was less than 5 ppm in all vehicles following vigorous shaking of the suspension for 25 days.

The solubility of Compound 1 was determined in vehicles containing 10 mM pH 7 phosphate buffer, 0.2% polysorbate 20 (PS), 0.8% saline, and various amounts of sorbitan monolaurate (SML). As shown in FIG. 2, Compound 1 showed increasing solubility with increasing SML concentration. At a given SML concentration, the trend of Compound 1 concentration as a function of pH is consistent with an estimated pKa of ~7. The total concentration of the hydrolysis products of Compound 1, aripiprazole and N-hydroxymethyl aripiprzole, was found to be less than 5 ppm in all vehicles following vigorous shaking of the suspension for 25 days. The degradation of dissolved Compound 1 was further followed in the drug vehicle containing 0.50% SML and 0.2% PS. Without being bound by theory, despite the increase in solubility, the observed slow degradation of Compound 1 at 25° C., 30° C. and 40° C. can be explained by higher solubility of Compound 1 in the organic droplets of SML as opposed to the aqueous portion of the vehicle.

FIG. 3 is a table showing in vitro (standing) studies of the pharmaceutical compositions described herein. This study was conducted at 25° C., with a relative humidity of 60%. The study demonstrated that the total concentration of the prodrug hydrolysis products did not exceed 6 ppm after 12 months of standing or 22 ppm after 24 months of standing.

FIG. 4 is a table showing in vitro (standing) studies of the pharmaceutical compositions described herein. This study was conducted at 30° C., with a relative humidity of 75%. The study demonstrated that the total concentration of the prodrug hydrolysis products did not exceed 16 ppm after 6 months of standing.

FIG. 5 is a table showing in vitro (standing) studies of the pharmaceutical compositions described herein. This study was conducted at 40° C., with a relative humidity of 75%. The study demonstrated that the total concentration of the prodrug hydrolysis products did not exceed 6 ppm after 12 months of standing or 22 ppm after 24 months of standing.

FIG. 6 is a table showing that there are low levels of aldehyde formation in the pharmaceutical compositions described herein. This study was conducted at 40° C., with a relative humidity of 75%.

Example II—Prodrug Synthesis Procedures

Synthesis of Aripiprazole Prodrugs

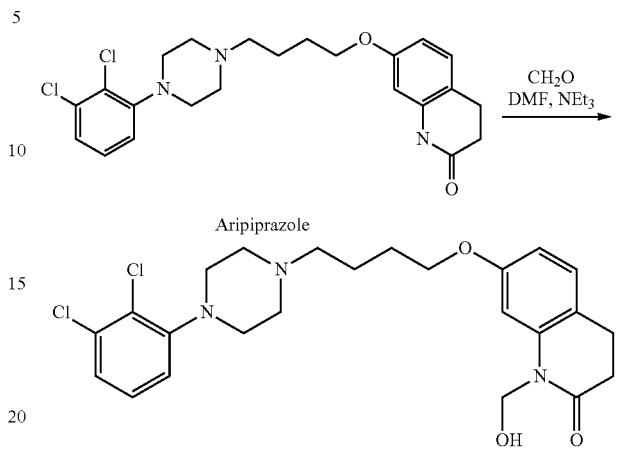

Compound A-1: Preparation of 7-(4-(4-(2,3-dichlorophenyl)piperazin-1-yl)butoxy)-1-(hydroxymethyl)-3,4-dihydroquinolin-2(1H)-one A mixture of Aripiprazole (20 g, 45 mmol), triethylamine (1 mL, 7.1 mmol), formaldehyde (37% aqueous solution, 70 mL) and dimethylformamide (200 mL) was heated to 80° C. for 20 h. The reaction mixture was cooled, diluted with ethyl acetate (400 mL) and washed with water/brine (1:1, 3×500 mL). The organic phase was dried over MgSO$_4$, filtered and evaporated to dryness under vacuum to give hemi-aminal A-1 as a white solid (18.6 g, containing 25% Aripiprazole, 65% yield based on A-1).

Compound 1: (7-(4-(4-(2,3-dichlorophenyl)piperazin-1-yl)butoxy)-2-oxo-3,4-dihydroquinolin-1(2H)-yl)methyl acetate

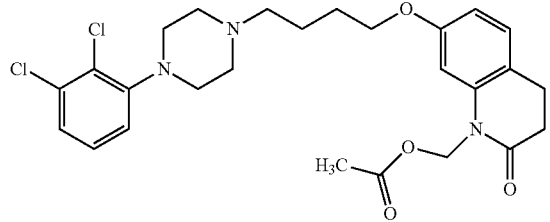 [SMILES: CC(=O)OCN1C(=O)CCc2ccc(OCCCCN3CCN(c4cccc(Cl)c4Cl)CC3)cc21]

A solution of Compound A-1 (50.63 g, 0.105 mol) in anhydrous tetrahydrofuran (THF, 80 mL) was treated with acetic anhydride (15.3 mL, 0.16 mol) and heated for 2.0 hours at 60° C. (oil-bath). To the above solution, triethylamine (2.0 mL, 0.014 mol) was added and stirred for 16 hours at 60° C. The solvent was removed using a rotator evaporator. To the resulting crude mixture, ethyl acetate (150 mL) and heptane (50 mL) was added. The solution was washed with NaHCO$_3$ (5% aqueous solution, 250 mL). After separation of the two layers, pH of the aqueous layer was adjusted to above 7. The aqueous layer was further extracted using the organic mixture. The organic layer was separated and washed with 5% NaHCO$_3$ solution, followed by deionized water, and brine. The solution was dried using anhydrous MgSO$_4$, filtered and evaporated under vacuum. The resulting product was purified using silica gel column chromatography using ethanol: ethyl acetate (5:95) as the eluent. Fractions containing the desired product were combined and d-tartaric acid (12.5 g dissolved in 60:5 ethanol: water) was added, resulting in the precipitation of the desired product (48.78 g, 89% yield). $^1$H NMR (CDCl3, 300 MHz) δ 1.73 (m, 2H), 1.84 (m, 2H), 2.12 (s, 3H), 2.50 (t, 2H), 2.68 (m, 6H), 2.87 (dd, 2H), 3.08 (m, 4H), 3.98 (t, 2H), 5.91 (s, 2H), 6.59 (m, 2H), 6.96 (dd, 1H), 7.08 (dd, 1H), 7.15 (m, 2H).

Compound 1: (7-(4-(4-(2,3-dichlorophenyl)piperazin-1-yl)butoxy)-2-oxo-3,4-dihydroquinolin-1(2H)-yl)methyl dodecanoate

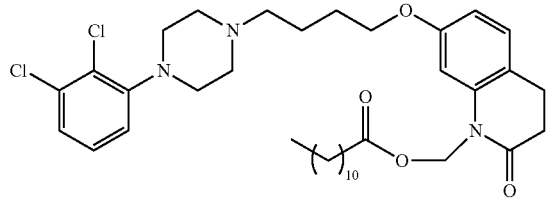

Compound 1 was prepared in an analogous fashion to Compound 1. The desired product was isolated as a crystalline solid (0.3 g, 21% yield). The molecular weight was confirmed by mass spectrometer analysis. FIG. 2-6 shows the PXRD, IR, Raman, TGA spectrum of the desired product. $^1$H NMR (CDCl3, 300 MHz) δ 0.87 (t, 3H), 1.24 (m, 16H), 1.62 (m, 2H), 1.83 (m, 2H), 1.86 (m, 2H), 2.36 (t, 2H), 2.49 (t, 2H), 2.68 (m, 6H), 2.86 (dd, 2H), 3.08 (m, 4H), 3.97 (t, 2H), 5.91 (s, 2H), 6.59 (m, 2H), 6.96 (dd, 1H), 7.07 (dd, 1H), 7.14 (m, 2H).

Compound A-28: (7-(4-(4-(2,3-dichlorophenyl)piperazin-1-yl)butoxy)-2-oxo-3,4-dihydroquinolin-1(2H)-yl)methyl benzylcarbamate

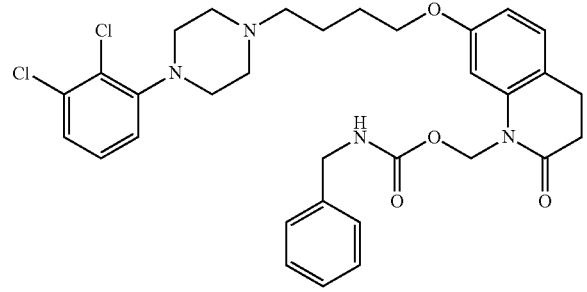 [SMILES: O=C(NCc1ccccc1)OCN1C(=O)CCc2ccc(OCCCCN3CCN(c4cccc(Cl)c4Cl)CC3)cc21]

To a solution of hemi-aminal A1 (4 g, 8.4 mmol), 4-dimethylaminopyridine (0.15 g, 1.3 mmol) and triethylamine (1.1 mL, 7.5 mmol) in dichloromethane (30 mL) was added benzylisocyanate (1.03 mL, 8.3 mmol) and the reaction mixture stirred for 24 hours. The reaction mixture was then heated at 35° C. for 20 hours, cooled and washed with water/brine (1:1, 50 mL). The organic phase was dried over MgSO$_4$, filtered and evaporated under vacuum. The residue was further purified by chromatography on silica eluting with ethyl acetate/dichloromethane/methanol (1:1:0.1) to give the desired product as an off white foam (530 mg, 14% yield). $^1$H NMR (CDCl$_3$, 300 MHz) δ 1.58-1.88 (m, 4H), 2.48 (t, 2H), 2.60-2.72 (m, 6H), 2.85 (m, 2H), 300-3.12 (m, 4H), 3.96 (t, 2H), 4.40 (d, 2H), 5.13 (NH), 5.96 (s, 2H), 6.58 (dd, 1H), 6.79 (d, 1H), 6.92-6.98 (m, 1H), 7.04 (d, 1H), 7.12-7.16 (m, 1H), 7.23-7.35 (m, 6H); m/z (M$^+$H) 611.12 and 613.10.

Compound A: (7-(4-(4-(2,3-dichlorophenyl)piperazin-1-yl)butoxy)-2-oxo-3,4-dihydroquinolin-1(2H)-yl)methyl hexanoate

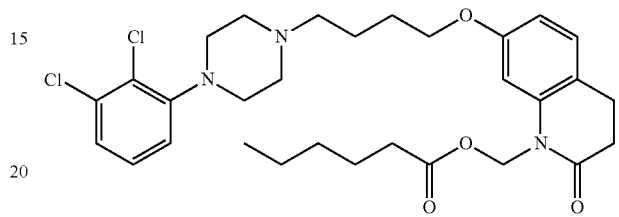

Compound A was prepared in an analogous fashion to Compound A-28. The desired product was isolated as a yellow solid (3.69 g, 87% yield). $^1$H NMR (CDCl$_3$, 300 MHz) δ 0.78 (t, 3H), 1.11-1.28 (m, 4H), 1.40-1.78 (m, 6H), 2.20-2.40 (m, 4H), 2.40-2.60 (m, 6H), 2.73-2.81 (m, 2H), 2.85-3.00 (m, 4H), 3.88-4.00 (m, 2H), 5.75-5.83 (m, 2H), 6.55-6.62 (m, 2H), 7.03-7.12 (m, 2H), 7.20-7.26 (m, 2H). m/z (M$^+$H) 576.4 and 578.4.

Olanzapine Prodrugs

Synthesis of chloromethyl 2-methyl-4-(4-methylpiperazin-1-yl)-5H-benzo[b]thieno[2,3-e][1,4]diazepine-5-carboxylate [A]

To a solution of olanzapine (18.0 g, 57.7 mmol) and triethylamine (16 mL, 0.12 mol) in dichloromethane (250 mL) was warmed to 35° C. and once a clear solution formed, the reaction was cooled to 5° C. To this was added chloromethyl chloroformate (7.6 mL, 86.5 mmol) over 20 minutes. The reaction was stirred at room temperature for 30 min and allowed to warm to room temperature. After 15 min at room temperature the reaction mixture was diluted with dichloromethane (100 mL), then washed with aq satd NaHCO$_3$ (75 mL) and water (350 mL). The organic phase was dried over MgSO$_4$ and filtered. The organic phase was then concentrated under vacuum at 45° C. to a volume of ~150 mL. The mixture was diluted with ethyl acetate (30 mL) and ~20-30 mL further was evaporated under vacuum. The mixture was cooled to room temperature and the resulting solid precipitate filtered and washed with ethyl acetate. After drying under vacuum at 35° C. for 90 min chloromethyl 2-methyl-4-(4-methylpiperazin-1-yl)-5H-benzo[b]thieno[2,3-e][1,4]diazepine-5-carboxylate [A] (17.1 g, 73%) was obtained as a yellow solid. $^1$H-NMR (300 MHz, CDCl$_3$) δ 7.62-7.14 (4H, m), 6.27-6.22 (1H, m), 5.84-5.69 (1H, m), 5.47-5.23 (1H, m), 3.89-3.63 (4H, m), 2.66-2.22 (10H, m).

General Procedure for the Synthesis of Aliphatic Carboxylic Acid Substituted Compounds Derived from [A]:

To a solution of chloromethyl 2-methyl-4-(4-methylpiperazin-1-yl)-5H-benzo[b]thieno[2,3-e][1,4]diazepine-5-carboxylate [A] (1 equiv) in dimethylformamide ((13 mL/g of [A])) was added cesium carbonate (1 equiv) and the appropriate aliphatic carboxylic acid (2 equiv). The reaction mixture was heated at 60° C. for 2-6 h, until starting material [A] had been consumed (loss of starting material determined by TLC). The reaction mixture was cooled, diluted with saturated aqueous NaHCO₃ (50 mL/g of [A]) and diethyl ether (75 mL/g of [A]). After being stirred for 15 min the mixture was filtered through celite and the organic phase separated. This was dried over MgSO₄ and evaporated. The residue was purified by column chromatography on silica eluting with 30% THF in EtOAc and the product containing fraction combined and evaporated. The residue was co-evaporated from hexanes.

Compound O-56: (palmitoyloxy)methyl 2-methyl-4-(4-methylpiperazin-1-yl)-5H-benzo[b]thieno[2,3-e][1,4]diazepine-5-carboxylate

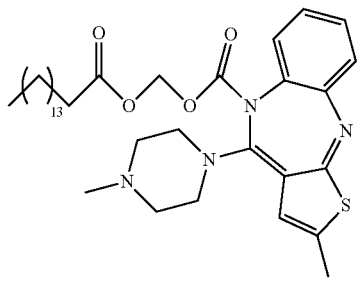

Using the procedure as described above with the exception of heating at 60° C. for 1 day gave (palmitoyloxy)methyl 2-methyl-4-(4-methylpiperazin-1-yl)-5H-benzo[b]thieno[2,3-e][1,4]diazepine-5-carboxylate (1.51 g, 75%) as a yellow oil. ¹H-NMR (300 MHz, CDCl₃) δ 7.62-7.55 (1H, m), 7.45-7.21 (2H, m), 7.17-7.08 (1H, m), 6.26-6.20 (1H, m), 5.66-5.35 (2H, m), 3.90-3.79 (2H, m), 3.68-3.54 (2H, m), 2.47-2.45 (4H, m), 2.33-2.24 (8H, m), 1.61-1.50 (2H, m), 1.35-1.15 (24H, m), 0.92-0.81 (3H, m)

Compound O-111: (stearoyloxy)methyl 2-methyl-4-(4-methylpiperazin-1-yl)-5H-benzo[b]thieno[2,3-e][1,4]diazepine-5-carboxylate

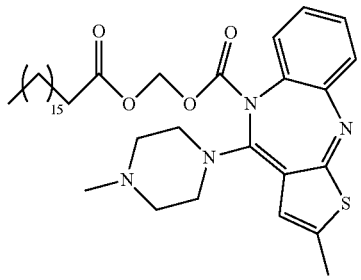

Using the procedure as described above gave (stearoyloxy)methyl 2-methyl-4-(4-methylpiperazin-1-yl)-5H-benzo[b]thieno[2,3-e][1,4]diazepine-5-carboxylate (1.51 g, 75%) as a yellow oil. ¹H-NMR (300 MHz, CDCl₃) δ 7.63-7.54 (1H, m), 7.46-7.37 (1H, m), 7.36-7.26 (1H, m), 7.18-7.07 (1H, m), 6.28-6.19 (1H, m), 5.67-5.56 (1.5H, m), 5.38-5.34 (1H, m), 3.91-3.78 (2H, m), 3.69-3.54 (2H, m), 2.50-2.40 (4H, m), 2.31-2.24 (6H, m), 1.61-1.50 (2H, s), 1.34-1.20 (30H, m), 0.87 (3H, t). [M+1-1]⁺=653.14.

Compound O-112: (icosanoyloxy)methyl 2-methyl-4-(4-methylpiperazin-1-yl)-5H-benzo[b]thieno[2,3-e][1,4]diazepine-5-carboxylate

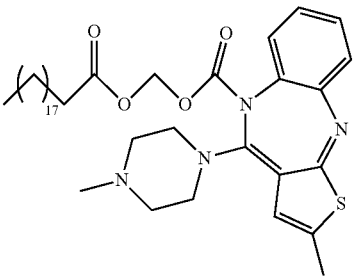

Using the procedure as described above gave (icosanoyloxy)methyl 2-methyl-4-(4-methylpiperazin-1-yl)-5H-benzo[b]thieno[2,3-e][1,4]diazepine-5-carboxylate (1.51 g, 75%) as a yellow oil. ¹H-NMR (300 MHz, CDCl₃) δ 7.63-7.54 (1H, m), 7.46-7.37 (1H, m), 7.36-7.26 (1H, m), 7.18-7.07 (1H, m), 6.28-6.19 (1H, m), 5.67-5.57 (1.5H, m), 5.37-5.34 (1H, m), 3.90-3.78 (2H, m), 3.69-3.53 (2H, m), 2.49-2.40 (4H, m), 2.32-2.24 (6H, m), 1.61-1.50 (2H, s), 1.34-1.20 (34H, m), 0.87 (3H, t). [M+11]⁺=681.19.

General Procedure for the Synthesis of Compounds 7-9

Synthesis of chloromethyl 2-methyl-4-(4-methylpiperazin-1-yl)-10H-benzo[b]thieno[2,3-e][1,4]diazepine-10-carboxylate [C]

To a solution of olanzapine (5.0 g, 16 mmol) in tetrahydrofuran (50 mL) at −78° C. was added tetramethylethylenediamine (2.4 mL, 16 mmol), followed by 2M n-BuLi in hexanes (8.0 mL, 16 mmol) over 5 min. The reaction mixture was stirred for 15 min and then chloromethyl chloroformate (2.1 mL, 24 mmol) added and the reaction mixture stirred a further 30 min. The reaction mixture was then warmed to room temperature, stirred for 1 h and quenched with water (50 mL). This mixture was diluted with brine (50 mL) and extracted with ethyl acetate (50 mL). The organic phase was dried over MgSO₄, evaporated and the residue further purified by column chromatography on silica eluting with 0.2:1:1 methanol/dichloromethane/ethyl acetate to give chloromethyl 2-methyl-4-(4-methylpiperazin-1-yl)-10H-benzo[b]thieno[2,3-e][1,4]diazepine-10-carboxylate [C] (5.6 g, ~50% pure by ¹H NMR and LCMS). This was used directly in the next reaction without further purification. ¹H-NMR (300 MHz, CDCl₃) δ 7.02-7.30 (4H, m), 6.45 (1H, s), 5.78-5.92 (1.5H, m), 5.52-5.60 (0.5H, m), 3.50-3.70 (4H, m), 2.35-2.55 (7H, m), 2.32 (3H, s). [M+11]⁺=405.0

General Procedure for the synthesis of aliphatic carboxylic acid substituted compounds derived from [C]:

To a solution of chloromethyl 2-methyl-4-(4-methylpiperazin-1-yl)-10H-benzo[b]thieno[2,3-e][1,4]diazepine-10-carboxylate (C:1 equiv) in dimethylformamide (13 mL/g of [C]) was added Cs₂CO₃ (1 equiv) and the appropriate aliphatic carboxylic acid (2 equiv). The reaction mixture was heated at 65° C. for 2-6 h, until starting material [A] had been consumed (loss of starting material determined by TLC). The reaction mixture was cooled, diluted with saturated aqueous NaHCO₃ (50 mL/g of [C]) and ethyl acetate (75 mL/g of [C]). After being stirred for 15 min the mixture was filtered through celite and the organic phase separated. This was dried over MgSO₄ and evaporated. The residue was further purified by column chromatography on silica eluting with 1:9 methanol/ethyl acetate and after evaporation of the product containing fractions, the residue was co-evaporated with hexane (2×10 mL/g [C]).

Compound O-7: (hexadecanoyloxy)methyl 2-methyl-4-(4-methylpiperazin-1-yl)-10H-benzo[b]thieno[2,3-e][1,4]diazepine-10-carboxylate

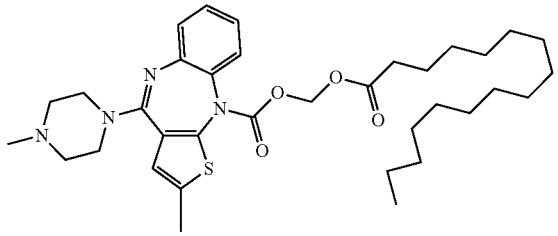 [SMILES: CCCCCCCCCCCCCCCC(=O)OCOC(=O)N1c2ccccc2N=C(N2CCN(C)CC2)c2cc(C)sc21]

Using the general procedure described above, employing palmitic acid and 1.0 g of the intermediate [C], provided (hexadecanoyloxy)methyl 2-methyl-4-(4-methylpiperazin-1-yl)-10H-benzo[b]thieno[2,3-e][1,4]diazepine-10-carboxylate (Compound O-7) (1.60 g, 39% yield) as a pale yellow oil. $^1$H-NMR (300 MHz, CDCl$_3$) δ 7.00-7.25 (4H, m), 6.43 (1H, s), 5.62-5.90 (2H, m), 3.51-3.66 (4H, m), 2.30-2.56 (10H, m), 1.58-1.68 (2H, m), 1.20-1.34 (26H), 0.87 (3H, t). [M+1-1]$^+$=625.07.

Compound O-8: (stearoyloxy)methyl 2-methyl-4-(4-methylpiperazin-1-yl)-10H-benzo[b]thieno[2,3-e][1,4]diazepine-10-carboxylate

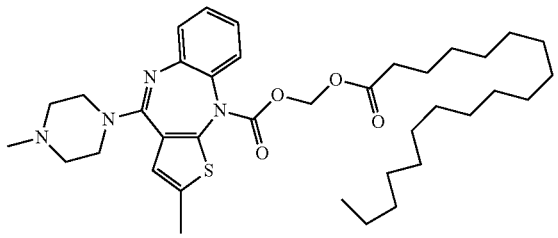 [SMILES: CCCCCCCCCCCCCCCCCC(=O)OCOC(=O)N1c2ccccc2N=C(N2CCN(C)CC2)c2cc(C)sc21]

Using the general procedure described above, employing stearic acid and 2.8 g of the intermediate [C], provided (stearoyloxy)methyl 2-methyl-4-(4-methylpiperazin-1-yl)-10H-benzo[b]thieno[2,3-e][1,4]diazepine-10-carboxylate (Compound O-8) (1.44 g, 32% yield) as a pale yellow oil. $^1$H-NMR (300 MHz, CDCl$_3$) δ 6.99-7.22 (4H, m), 6.43 (1H, s), 5.62-5.88 (2H, m), 3.51-3.66 (4H, m), 2.30-2.66 (10H, m), 1.55-1.70 (2H, m), 1.20-1.34 (30H), 0.87 (3H, t). [M+H]$^+$=653.21.

Compound O-9: (arachidoyloxy)methyl 2-methyl-4-(4-methylpiperazin-1-yl)-10H-benzo[b]thieno[2,3-e][1,4]diazepine-10-carboxylate

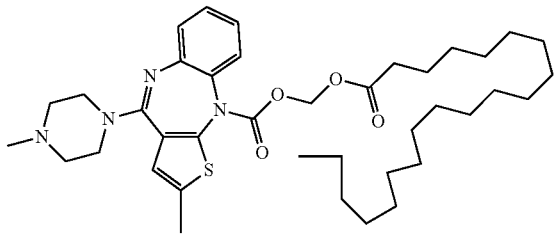 [SMILES: CCCCCCCCCCCCCCCCCCCC(=O)OCOC(=O)N1c2ccccc2N=C(N2CCN(C)CC2)c2cc(C)sc21]

Compound O-9 can be made using the general procedure described above, and by employing arachidic acid and the intermediate [C], which could then provide (arachidoyloxy)methyl 2-methyl-4-(4-methylpiperazin-1-yl)-10H-benzo[b]thieno[2,3-e][1,4]diazepine-10-carboxylate (Compound O-9).

Example III—Exemplary Aripiprazole Prodrug Formulation

| Formulation | Amount Per Dose (% w/w) |
|---|---|
| Compound I | 26.6 |
| Sorbitan monolaurate | 0.37 |
| Polysorbate 20 | 0.15 |
| Sodium Chloride | 0.59 |
| CMC | NA |
| Sodium Phosphate Dibasic Anhydrous | 0.06 |
| Sodium Dihydrogen Phosphate Monobasic Dihydrate | 0.05 |
| Water for Injection | QS to 100 | pH range: 5.0-7.4

INCORPORATION BY REFERENCE

The entire contents of all patents, published patent applications, and other references cited herein are hereby expressly incorporated herein in their entireties by reference.

The invention claimed is:

1. A pharmaceutical composition comprising:
(a) Compound 1

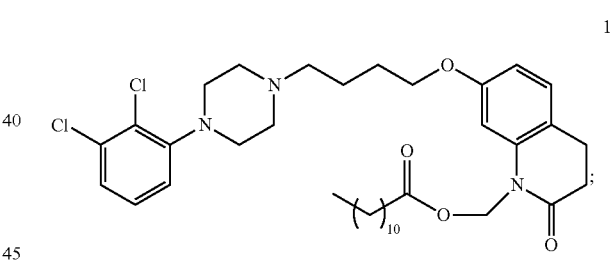

(b) a non-ionic water insoluble and/or immiscible ester co-surfactant that is a sorbitan ester of a carboxylic acid, wherein the carboxylic acid comprises 4-20 carbon atoms;
(c) a water miscible and/or soluble non-ionic surfactant; and
(d) an aqueous vehicle;
wherein the pharmaceutical composition comprises less than 50 parts per million of the hydrolysis product of Compound 1.

2. The pharmaceutical composition of claim 1, wherein the pharmaceutical composition comprises less than 30 parts per million of the hydrolysis product of Compound 1 after standing for at least 24 months.

3. The pharmaceutical composition of claim 1, wherein the water miscible and/or soluble non-ionic surfactant is a polyoxyethylene derivative of a sorbitan ester of a carboxylic acid, wherein the carboxylic acid comprises 8-14 carbon atoms.

4. The pharmaceutical composition of claim 1, wherein the sorbitan ester is sorbitan laurate.

5. The pharmaceutical composition of claim 3, wherein the polyoxyethylene derivative of a sorbitan ester is polysorbate 20.

6. A pharmaceutical composition comprising:
(a) 20-30 weight percent compound I:

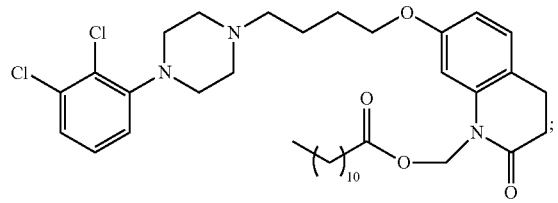

(b) about 0.2-1 weight percent sorbitan laurate;
(c) about 0.1-0.3 weight percent polysorbate 20; and
(d) an aqueous vehicle;
wherein the pharmaceutical composition comprises less than 50 parts per million of the hydrolysis product of Compound 1.

7. A method of treating schizophrenia in a subject in need thereof comprising administering to the subject the composition of claim 1.

8. A method of treating schizophrenia in a subject in need thereof comprising administering to the subject the composition of claim 6.

9. A method of treating bipolar disorder in a subject in need thereof comprising administering to the subject the composition of claim 6.

10. A method of treating anxiety in a subject in need thereof comprising administering to the subject the composition of claim 6.

11. A method of treating depression in a subject in need thereof comprising administering to the subject the composition of claim 6.

12. A method of treating autism-related irritability in a subject in need thereof comprising administering to the subject the composition of claim 6.

13. A method of treating acute mania in a subject in need thereof comprising administering to the subject the composition of claim 6.

14. The pharmaceutical composition of claim 1, wherein the hydrolysis product of Compound 1 is:

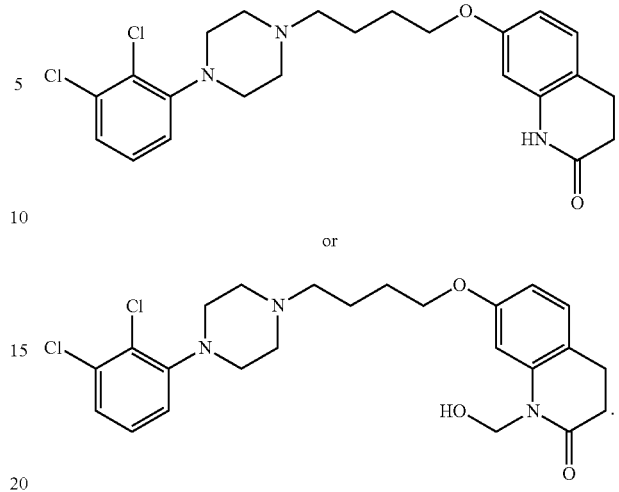

15. The pharmaceutical composition of claim 6, wherein the hydrolysis product of Compound 1 is:

* * * * *